US012583860B2

(12) United States Patent
Stirk et al.

(10) Patent No.: US 12,583,860 B2
(45) Date of Patent: Mar. 24, 2026

(54) PROCESSES FOR THE PREPARATION OF MULTICOMPONENT CRYSTALLINE FORMS OF ACTIVE PHARMACEUTICAL INGREDIENTS USING SOLVENT VAPOUR

(71) Applicant: Apotex Inc., Toronto (CA)

(72) Inventors: Alexander J. Stirk, Dartmouth (CA); Fabio E. S. Souza, Mississauga (CA); Avedis Karadeolian, Brantford (CA); Allan W. Rey, Toronto (CA); Fatemeh Mohammadpourmir, Canton, MI (US)

(73) Assignee: Apotex Inc., Toronto (CA)

( * ) Notice: Subject to any disclaimer, the term of this patent is extended or adjusted under 35 U.S.C. 154(b) by 797 days.

(21) Appl. No.: 17/802,203

(22) PCT Filed: Feb. 24, 2021

(86) PCT No.: PCT/CA2021/050218
§ 371 (c)(1),
(2) Date: Aug. 25, 2022

(87) PCT Pub. No.: WO2021/168561
PCT Pub. Date: Sep. 2, 2021

(65) Prior Publication Data
US 2024/0010651 A1     Jan. 11, 2024

Related U.S. Application Data

(60) Provisional application No. 63/093,481, filed on Oct. 19, 2020, provisional application No. 62/981,817, filed on Feb. 26, 2020.

(51) Int. Cl.
*C07D 487/04*     (2006.01)
*A61K 31/10*     (2006.01)
(Continued)

(52) U.S. Cl.
CPC ............ *C07D 487/04* (2013.01); *A61K 31/10* (2013.01); *A61K 31/352* (2013.01);
(Continued)

(58) Field of Classification Search
CPC .. C07D 487/04; C07B 2200/13; A61K 31/10; A61K 31/4985; A61K 2300/00
(Continued)

(56) References Cited

U.S. PATENT DOCUMENTS 10,183,024 B2     1/2019  Souza et al.
10,513,500 B2     12/2019  Gerster et al.
(Continued)

FOREIGN PATENT DOCUMENTS

CA      2500676 A1     9/2006
WO      2006094396 A1     9/2006
(Continued)

OTHER PUBLICATIONS

Boldyreva E. Mechanochemistry of inorganic and organic systems: what is similar, what is different?. Chemical Society Reviews. 2013;42(18):7719-38. (Year: 2013).*
(Continued)

*Primary Examiner* — Jeffrey S Lundgren
*Assistant Examiner* — Heather Dahlin
(74) *Attorney, Agent, or Firm* — The Webb Law Firm

(57)     ABSTRACT

The present invention provides solvent-limited processes for the preparation of an existing crystalline solid form of an active pharmaceutical ingredient comprising mixing, in the presence of solvent vapour, of a solid active pharmaceutical ingredient and a pharmaceutically acceptable entity that is either a high-boiling liquid or a solid. Also provided is the use of a standard rotary apparatus, such as a rotary cone dryer, for application of the processes herein.

14 Claims, 13 Drawing Sheets

(51) Int. Cl.

| | |
|---|---|
| *A61K 31/352* | (2006.01) |
| *A61K 31/675* | (2006.01) |
| *C07C 69/78* | (2006.01) |
| *C07C 275/02* | (2006.01) |
| *C07D 213/82* | (2006.01) |
| *C07D 311/30* | (2006.01) |
| *C07D 471/04* | (2006.01) |

(52) U.S. Cl.
    CPC ............ *A61K 31/675* (2013.01); *C07C 69/78* (2013.01); *C07C 275/02* (2013.01); *C07D 213/82* (2013.01); *C07D 311/30* (2013.01); *C07D 471/04* (2013.01); *C07B 2200/13* (2013.01)

(58) Field of Classification Search
    USPC ........................................................ 514/81
    See application file for complete search history.

(56) References Cited

U.S. PATENT DOCUMENTS

| | | | |
|---|---|---|---|
| 2006/0205944 A1 | 9/2006 | Rey et al. | |
| 2006/0205947 A1 | 9/2006 | Rey et al. | |
| 2018/0346504 A1* | 12/2018 | Brak ..................... | C07H 19/00 |
| 2019/0112299 A1 | 4/2019 | Souza et al. | |
| 2019/0263760 A1 | 8/2019 | Gerster et al. | |
| 2019/0343815 A1 | 11/2019 | Souza et al. | |

FOREIGN PATENT DOCUMENTS

| | | | |
|---|---|---|---|
| WO | 2012081031 A1 | 6/2012 |
| WO | 2012092395 A2 | 7/2012 |
| WO | 2013184572 A1 | 12/2013 |
| WO | 2017002095 A1 | 1/2017 |
| WO | 2018085932 A1 | 5/2018 |
| WO | 2018204198 A1 | 11/2018 |
| WO | 2019041026 A1 | 3/2019 |

OTHER PUBLICATIONS

National Center for Biotechnology Information (2025). PubChem Compound Summary for CID 867, Malonic acid. Retrieved May 19, 2025. (Year: 2004).*

Ji C, Hoffman MC, Mehta MA. Catalytic effect of solvent vapors on the spontaneous formation of caffeine-malonic acid cocrystal. Crystal Growth & Design. Apr. 5, 2017;17(4):1456-9. (Year: 2017).*

Cowell, A., 2011. An investigation into the synthesis, structural characterisation, thermal and polymorphic behaviour of organic crystalline materials (Doctoral dissertation, University of Birmingham). (Year: 2011).*

Braga et al., "Solvent effect in a "solvent free" reaction", CrystEngComm, 2007, pp. 879-881, vol. 9.

Cox et al., "The Structure of alpha-Oxalic Acid and of the Carboxyl Group", A. J. Chem. Soc., 1952, pp. 4854-4864.

Stahl et al., "Handbook of Pharmaceutical Salts Properties, Selection, and Use", International Union of Pure and Applied Chemistry (IUPAC), 2002, pp. 329-345.

Huskic et al., "Accelerated ageing reactions: towards simpler, solvent-free, low energy chemistry", Green Chem., 2020, pp. 1-21, vol. 22.

Jayasankar et al., "Mechanisms by Which Moisture Generates Cocrystals", Molecular Pharmaceutics, 2007, pp. 360-372, vol. 4, No. 3.

Ji et al., "Catalytic Effect of Solvent Vapors on the Spontaneous Formation of Caffeine-Malonic Acid Cocrystal", Cryst. Growth Des., 2017, pp. 1456-1459, vol. 17.

Karimi-Jafari et al., "Creating Cocrystals: A Review of Pharmaceutical Cocrystal Preparation Routes and Applications", Cryst. Growth Des. 2018, pp. 6370-6387, vol. 18.

Ravikumar et al., "Olazipinium nicotinate", Acta Cryst. 2005, pp. o2720-o2723, vol. E61.

Rodrigues et al., "Pharmaceutical cocrystallization techniques. Advances and challenges", International Journal of Pharmaceutics, 2018, pp. 404-420, vol. 547.

Rossi et al., "The Crystal and Molecular Structure of Quercetin: A Biologically Active and Naturally Occurring Flavonoid", Bioorg. Chem., 1986, pp. 55-69, vol. 14.

Sarcevica et al., "Mechanistic and kinetic insight into spontaneous cocrystallisation of isoniazid and benzoic acid", Mol. Pharmaceutics, 2015, pp. 2981-2992, vol. 12.

Sarcevica et al., "Isoniazid cocrystallisation with dicarboxylic acids: vapochemical, mechanochemical and thermal methods", CrystEngComm, 2016, pp. 1625-1635, vol. 18.

Shahat, "The Crystal and Molecular Structure of Maleic Acid", Acta Cryst., 1952, pp. 763-768, vol. 5.

Sklar et al., "Thermal Effects in Urea: The Crystal Structure at −140oC. and at Room Temperature", Acta Cryst., 1961, pp. 716-720, vol. 14.

Wright et al., "The crystal structure of nicotinamide", Acta Cryst., 1954, pp. 283-288, vol. 7.

* cited by examiner

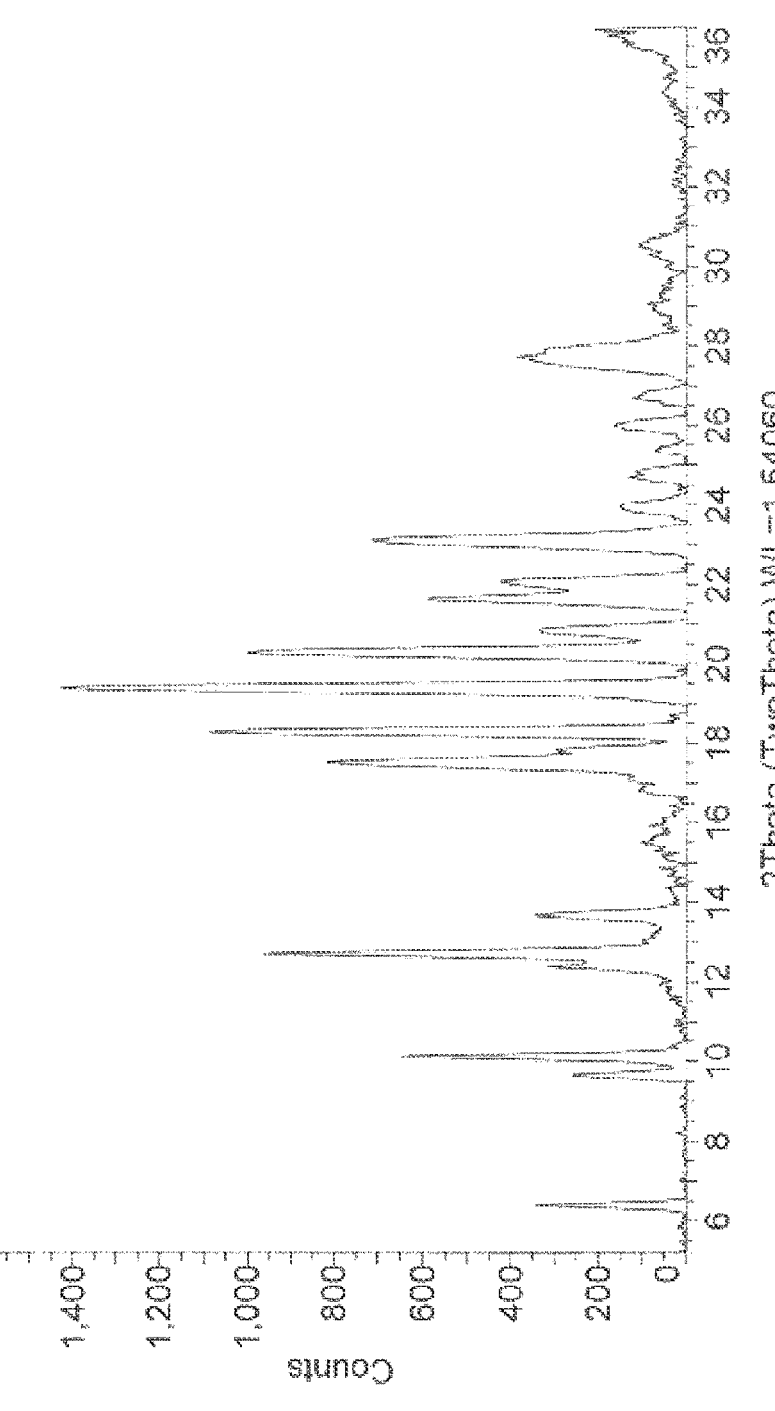
FIG. 6

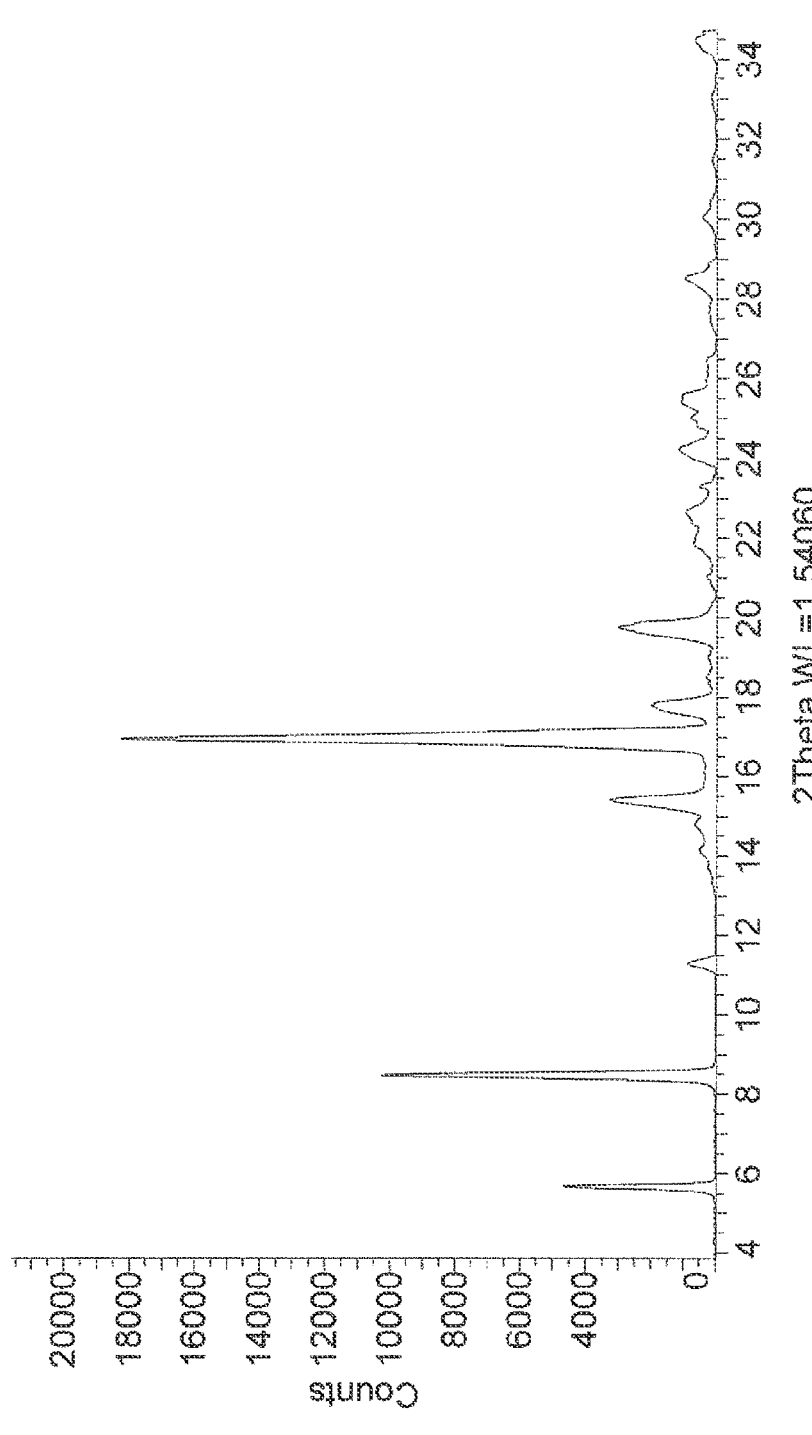

PROCESSES FOR THE PREPARATION OF MULTICOMPONENT CRYSTALLINE FORMS OF ACTIVE PHARMACEUTICAL INGREDIENTS USING SOLVENT VAPOUR

CROSS-REFERENCE TO RELATED APPLICATIONS

This application is the United States national phase of International Application No. PCT/CA2021/050218 filed Feb. 24, 2021, and claims priority to United States Provisional Patent Application Nos. 62/981,817 filed Feb. 26, 2020 and 63/093,481 filed Oct. 19, 2020, the disclosures of which are hereby incorporated by reference in their entireties.

BACKGROUND OF THE INVENTION

Field of the Invention

The present invention is directed to novel processes for the preparation of crystalline solid forms of active pharmaceutical ingredients and to the use of an apparatus therefor.

Description of Related Art

Active pharmaceutical ingredients (APIs) often exist as solids under ambient conditions, and solid forms of active pharmaceutical ingredients, whether neutral compounds or salts thereof, can generally be classified as amorphous, crystalline, or as a mixture thereof. Amorphous solids lack long-range packing order and do not have a distinguishable crystal lattice whereas crystalline solids exhibit a regular and repeating packing array of a structural unit (i.e. unit cell) and include salts, polymorphs, solvates, hydrates, and cocrystals. Polymorphs of a substance such as an API adopt different packing arrangements and/or conformations in the repeating unit of the crystal structure. Solvates, hydrates, and cocrystals are multiple-component crystalline forms which are composed of two or more distinct components incorporated into the crystal structure. In a solvate of an API, the crystal structure includes both the API and a solvent molecule(s) whereas when the solvent that is incorporated into the crystal structure is water, the solid form is referred to more specifically as a hydrate. Cocrystals are composed of a stoichiometric ratio of two or more different molecular and/or ionic compounds in a single-phase crystal lattice, for example an API and a 'coformer', which are neither solvates nor salts. Unlike salts, the components of cocrystals are held together by non-covalent interactions such as hydrogen bonds, π-π interactions, and van der Waals forces. Within these broad categories of crystalline solids, it is possible to have overlap. For example, a cocrystal substance comprised of an API and a coformer may also exist in various polymorphic forms, hydrate forms, and solvate forms.

The ionization state of a substance and the nature of the solid form are important determinants of its physicochemical and biopharmaceutical properties such as solubility, dissolution rate, bioavailability, chemical and physical stability, hygroscopicity and mechanical attributes. Such properties can be critical to the viability of an API, which must possess an acceptable balance of favourable physicochemical attributes to establish its safety and efficacy with important regulatory authorities such as the U.S. Food & Drug Administration (FDA).

Salt formation is the most commonly used method of altering the physicochemical properties of an API, particularly in relation to improving dissolution rate and bioavailability. Apart from the alteration of properties that is possible through salt formation, the popularity of pharmaceutical salts also arises from the identification of a finite number of pharmaceutically suitable counterions and the established regulatory pathway for approval of salts.

Interest in multiple-component crystalline forms of APIs, particularly cocrystals, has grown substantially in the last decade. One reason for this growth is due to the unique alteration of properties that is possible when a coformer is incorporated into the crystal structure of the API. For example, cocrystals of an API comprised of a water-soluble coformer can exhibit markedly improved aqueous solubility and bioavailability compared to non-cocrystal solid forms of the API. Additionally, unlike salts, cocrystals can be prepared from non-ionizable APIs. Furthermore, the pool of suitable non-toxic coformer candidates is much larger than the number of pharmaceutically acceptable salt counterions.

Several FDA-approved drug products have been categorized as cocrystals, including ENTRESTO®, a multi-drug cocrystal formed between sacubitril and valsartan, LEXAPRO®, a cocrystal of escitalopram oxalate salt comprising a cocrystallised oxalic acid molecule, and DEPAKOTE®, a cocrystal of sodium valproate and valproic acid.

Multiple-component crystalline forms comprising APIs have also been reported in, for example, WO 2019/041026 A1, U.S. Pat. Nos. 10,183,024 B2, 10,513,500 B2, US 2019/112299 A1, and US 2019/0343815 A1. For example, WO 2019/041026 A1 discloses cocrystals of acalabrutinib with urea, nicotinamide, and L-sorbitol; US B2 discloses solvates of ibrutinib with methyl benzoate and methyl salicylate; U.S. Pat. No. 10,513,500 B2 reports a cocrystal of lesinurad and nicotinamide; US 2019/112299 A1 describes a cocrystal of lumacaftor and nicotinamide; and US 2019/0343815 A1 discloses cocrystals of deutetrabenazine (and tetrabenazine) with quercetin and luteolin. It is reported that these crystalline forms offer advantages compared to other forms of the same APIs including, for example, enhanced solubility, enhanced physical/chemical stability and/or regulatory acceptability of incorporated components. In each case, the crystalline forms are prepared by solvent-based methods in these documents.

Methods for the preparation of salts and cocrystals can be classified broadly as either solvent-based methods, which utilize solvent as a medium for salt or cocrystal formation, or as solid-state methods, which utilize negligible amounts of solvent or which are solvent-free. Solvent-based methods include evaporative crystallization, spray-drying, slurry conversion, cooling crystallization, reactive crystallization, anti-solvent crystallization, and supercritical fluid crystallization. Solid-state methods, more commonly employed in the formation of cocrystals, include contact formation, neat-grinding, liquid-assisted grinding (LAG), melt extrusion, high shear wet granulation, and extrusion. A review of cocrystal preparation routes, several of which are also applicable to the preparation of salts, is provided in Karimi-Jafari et al. *Cryst. Growth Des.* 2018, 18, 6370-6387.

Despite the promise of multiple-component crystalline forms of APIs, and cocrystals in particular, one key challenge hampering widespread use of these materials is the relative lack of scalable industrial production methods. Though solvent-based methods of cocrystal formation such as spray-drying and solvent cocrystallization are considered scalable for industrial production, the requirement for relatively large volumes of solvent and the necessity of determining the concentration range wherein the cocrystal is stable detract from the usefulness of these processes.

There are advantages associated with the use of solid-state methods in the preparation of both salts and multiple-component crystalline forms such as cocrystals. Foremost is the essential elimination of solvent, which positively impacts several areas of concern related to the production of an API including environmental impact, safety, cost, and regulatory acceptability. Furthermore, solid-state methods are often quantitative, as yield is not lost due to the solubilization of the components in a solvent. However, reported scalable solid-state salt and cocrystal formation methods such as extrusion and granulation suffer from the requirement for specialized and costly equipment not typically utilized in an API production environment, such as screw extruders.

One rarely reported solid-state method for preparing cocrystals is by simple contact between a compound and a coformer or by contact accompanied by exposure to water or solvent vapour, referred to as vapour digestion. Examples of preparation of cocrystals by contact formation, including vapour digestion, are described in Braga et al. *CrystEngComm* 2007, 9, 879-881, Jayasankar et al. *Mol. Pharmaceutics* 2017, 4(3), 360-372, Sarcevica et al. *Mol. Pharmaceutics* 2015, 12, 2981-2992, Ji et al. *Cryst. Growth Des.* 2017, 17, 1456-1459 and Huskic, I.; Lennox, C.; and Friši, T. *Green Chem.* 2020, 22, 5881-5901. These research publications are oriented to the academic study of the factors and mechanism of cocrystal formation by contact and vapour digestion. As such, the methods and equipment that are employed are generally ad hoc assemblies which are not amenable to application on an industrial scale.

There exists a need for novel and industrially applicable solid-state methods for the preparation of pharmaceutical salts and multiple-component crystalline forms.

SUMMARY OF THE INVENTION

The present invention provides processes for the preparation of an existing crystalline solid form of an active pharmaceutical ingredient and a pharmaceutically acceptable entity comprising mixing, in the presence of solvent vapour, of the active pharmaceutical ingredient in solid form and the entity in the form of either a high-boiling liquid or a solid and which is incorporated into the crystal lattice with the active pharmaceutical ingredient. In one embodiment of the present invention, the entity is a coformer and the crystalline solid form is a multiple-component crystalline form of the active pharmaceutical ingredient, such as a cocrystal. In another embodiment, the entity is an acid or a base and the crystalline solid form is a salt of the active pharmaceutical ingredient. Due to the limited usage of solvent, the processes of the present invention can be considered 'green', which not only reduces environmental impact but also results in cost-savings in relation to lower consumption of goods and reduced solvent waste disposal charges. In addition, the use of solvent vapour rather than liquid solvent affords solids having low levels of residual solvent, which is critical to the regulatory acceptability of APIs, as governed by the ICH (International Council for Harmonisation of Technical Requirements for Pharmaceuticals for Human Use). Further, the processes of the present invention are simple and can be conducted in standard production equipment commonly employed in the pharmaceutical industry, such as a rotary cone dryer.

Accordingly, in a first aspect of the present invention, there is provided a process for the preparation of an existing crystalline solid form comprising an active pharmaceutical ingredient and a distinct pharmaceutically acceptable entity, the process comprising mixing, in the presence of solvent vapour, of:

(i) the active pharmaceutical ingredient in solid form; and
(ii) the pharmaceutically acceptable entity, in solid or liquid form, wherein the entity has a melting point greater than approximately 30° C. or a boiling point greater than approximately 150° C. and the pharmaceutically acceptable entity and active pharmaceutical ingredient are incorporated in the same crystalline lattice.

In a preferred embodiment of the first aspect, the mixing is conducted in a stationary apparatus by means of an agitator device operable inside of a stationary vessel containing the active pharmaceutical ingredient and the entity. Preferably, the stationary apparatus comprises: a stationary vessel defining a chamber for mixing of the active pharmaceutical ingredient and the entity; an aperture in the stationary vessel enabling communication between the chamber and a source of solvent vapour; an agitator device that is operable inside of the stationary vessel for mixing; and a means for operating the agitator device. More preferably, the agitator device is selected from the group consisting of a screw, blade, ribbon, and paddle. In a further preferred embodiment of the first aspect, the solvent vapour is delivered through a first aperture in the vessel and evacuated through a second aperture in the vessel that is spaced from the first aperture.

In a further preferred embodiment of the first aspect, the mixing is conducted in a rotary apparatus by means of rotation of a vessel containing the active pharmaceutical ingredient and the entity about its own axis. Preferably, the vessel has a shape that is selected from the group consisting of a cylindrical shape, a spherical shape, a cubic shape, a double-cone shape, a v-shape, a y-shape, and a diamond-shape. In another preferred embodiment, the rotary apparatus comprises: a fixed support structure; a vessel rotatably supported by the fixed support structure about an axis and defining a chamber for mixing of the active pharmaceutical ingredient and the entity; an aperture in the vessel enabling communication between the chamber and a source of solvent vapour; and means for rotating the vessel about the axis. In a further preferred embodiment, the vessel is a double-cone shape, formed from the connection of two frusta across their major bases with the interception of a circular cylindrical connector. In a further preferred embodiment, the solvent vapour is delivered through a first aperture in the vessel and evacuated through a second aperture in the vessel that is spaced from the first aperture.

In a further preferred embodiment of the first aspect, the solvent vapour is generated by passing an inert gas through liquid solvent.

In another preferred embodiment of the first aspect, the solvent is selected from the group consisting of ketones, alcohols, and esters. Preferably, the solvent is selected from the group consisting of acetone, ethyl acetate, methanol, and ethanol. Most preferably, the solvent is acetone.

In a further preferred embodiment of the first aspect, the entity is a coformer and the crystalline solid form is a multiple-component crystalline form.

In another preferred embodiment of the first aspect, the multiple-component crystalline form is a cocrystal of an active pharmaceutical ingredient and nicotinamide. Preferably, the active pharmaceutical ingredient is selected from the group consisting of acalabrutinib, lumacaftor, and lesinurad.

In another preferred embodiment of the first aspect, the multiple-component crystalline form is a cocrystal of acalabrutinib and a coformer having a melting point greater than approximately 30° C.

In a further preferred embodiment of the first aspect, the multiple-component crystalline form is selected from the group consisting of: a cocrystal of acalabrutinib and urea; a cocrystal of acalabrutinib and nicotinamide; a solvate of ibrutinib and methyl benzoate; a cocrystal of ibrutinib and methyl nicotinate; a cocrystal of tetrabenazine and quercetin; a cocrystal of lesinurad and nicotinamide; and a cocrystal of lumacaftor and nicotinamide.

In another preferred embodiment of the first aspect, the multiple-component crystalline form is a cocrystal of acalabrutinib and urea having a molar ratio of acalabrutinib to urea of approximately 1:2. Preferably, the multiple-component crystalline form is characterized by a PXRD diffractogram comprising peaks, expressed in degrees 2θ (±0.2°), at 5.4°, 6.6° and 11.0°. More preferably, the PXRD diffractogram further comprises at least three peaks, expressed in degrees 2θ (±0.2°), selected from the group consisting of: 10.1°, 13.2°, 15.1°, 17.3°, 19.9°, 21.1° and 22.2°. Most preferably, the PXRD diffractogram further comprises peaks, expressed in degrees 2θ (±0.2°), at 10.1°, 13.2°, 15.1°, 17.3°, 19.9°, 21.1° and 22.2°.

In another preferred embodiment of the first aspect, the multiple-component crystalline form is a cocrystal of acalabrutinib and nicotinamide having a molar ratio of acalabrutinib to nicotinamide of approximately 1:2. Preferably, the multiple-component crystalline form is characterized by a PXRD diffractogram comprising peaks, expressed in degrees 2θ (±0.2°), at 5.8°, 7.2° and 14.6°. More preferably, the PXRD diffractogram further comprises at least three peaks, expressed in degrees 2θ (±0.2°), selected from the group consisting of: 9.2°, 10.2°, 11.4°, 12.8°, 16.0°, 18.5°, 21.1°, 21.9°, 23.4° and 24.1°. Most preferably, the PXRD diffractogram further comprises peaks, expressed in degrees 2θ (±0.2°), at 9.2°, 10.2°, 11.4°, 12.8°, 16.0°, 18.5°, 21.1°, 21.9°, 23.4° and 24.1°.

In another preferred embodiment of the first aspect, the multiple-component crystalline form is a solvate of ibrutinib and methyl benzoate having a molar ratio of ibrutinib to methyl benzoate of approximately 1:0.5. Preferably, the multiple-component crystalline form is characterized by a PXRD diffractogram comprising peaks, expressed in degrees 2θ (±0.2°), at 6.4°, 10.1° and 12.8°. More preferably, the PXRD diffractogram further comprises at least three peaks, expressed in degrees 2θ (±0.2°), selected from the group consisting of: 13.8°, 17.6°, 18.4°, 19.4°, 20.4°, 21.0°, 21.7°, 23.2°, 24.1° and 24.9°. Most preferably, the PXRD diffractogram further comprises peaks, expressed in degrees 2θ (±0.2°), at 13.8°, 17.6°, 18.4°, 19.4°, 20.4°, 21.0°, 21.7°, 23.2°, 24.1° and 24.9°.

In another preferred embodiment of the first aspect, the multiple-component crystalline form is a cocrystal of ibrutinib and methyl nicotinate having a molar ratio of ibrutinib to methyl nicotinate of approximately 1:0.5. Preferably, the multiple-component crystalline form is characterized by a PXRD diffractogram comprising peaks, expressed in degrees 2θ (±0.2°), at 6.4°, 10.1° and 12.7°. More preferably, the PXRD diffractogram further comprises at least three peaks, expressed in degrees 2θ (±0.2°), selected from the group consisting of: 9.7°, 13.7°, 17.5°, 18.3°, 19.4°, 20.3°, 20.8°, 21.6°, 22.0° and 23.1°. Most preferably, the PXRD diffractogram further comprises peaks, expressed in degrees 2θ (±0.2°), at 9.7°, 13.7°, 17.5°, 18.3°, 19.4°, 20.3°, 20.8°, 21.6°, 22.0° and 23.1°.

In another preferred embodiment of the first aspect, the multiple-component crystalline form is a cocrystal of tetrabenazine and quercetin having a molar ratio of tetrabenazine to quercetin of approximately 1:1. Preferably, the multiple-component crystalline form is characterized by a PXRD diffractogram comprising peaks, expressed in degrees 2θ (±0.2°), at 6.3°, 9.4° and 14.3°. More preferably, the PXRD diffractogram further comprises at least three peaks, expressed in degrees 2θ (±0.2°), selected from the group consisting of: 7.0°, 10.4°, 11.1°, 12.5°, 15.8° and 18.8°. Most preferably, the PXRD diffractogram further comprises peaks, expressed in degrees 2θ (±0.2°), at 7.0°, 11.1°, 12.5°, 15.8° and 18.8°.

In another preferred embodiment of the first aspect, the multiple-component crystalline form is a cocrystal of lesinurad and nicotinamide having a molar ratio of lesinurad to nicotinamide of approximately 1:1. Preferably, the multiple-component crystalline form is characterized by a PXRD diffractogram comprising peaks, expressed in degrees 2θ (±0.2°), at 6.2° and 19.9°. More preferably, the PXRD diffractogram further comprises at least three peaks, expressed in degrees 2θ (±0.2°), selected from the group consisting of: 7.6°, 10.3°, 14.1°, 15.3°, 17.8°, 21.1°, 23.4°, 25.7° and 27.2°. Most preferably, the PXRD diffractogram further comprises peaks, expressed in degrees 2θ (±0.2°), at 7.6°, 10.3°, 14.1°, 15.3°, 17.8°, 21.1°, 23.4°, 25.7° and 27.2°.

In another preferred embodiment of the first aspect, the multiple-component crystalline form is a cocrystal of lumacaftor and nicotinamide having a molar ratio of lumacaftor to nicotinamide of approximately 1:2. Preferably, the multiple-component crystalline form is characterized by a PXRD diffractogram comprising peaks, expressed in degrees 2θ (±0.2°), 5.7°, 8.5° and 17.0°. More preferably, the PXRD diffractogram further comprises at least three peaks, expressed in degrees 2θ (±0.2°), selected from the group consisting of: 11.3°, 15.4°, 17.8° and 19.8°. Most preferably, the PXRD diffractogram further comprises peaks, expressed in degrees 2θ (±0.2°), at 11.3°, 15.4°, 17.8° and 19.8°.

In a further preferred embodiment of the first aspect, the entity is an acid or a base and the crystalline solid form is a salt.

In another preferred embodiment of the first aspect, the active pharmaceutical ingredient is an amine and the entity is an acid having a melting point greater than approximately 30° C. Preferably, the acid is selected from the group consisting of fumaric acid, maleic acid, L-malic acid, succinic acid, citric acid, L-tartaric acid, oxalic acid, and naphthalene-2-sulfonic acid. In a more preferred embodiment, the active pharmaceutical ingredient is remdesivir and the entity is selected from the group consisting of maleic acid, oxalic acid, and naphthalene-2-sulfonic acid.

In another preferred embodiment of the first aspect, the salt is a napsylate salt of remdesivir having a molar ratio of remdesivir to naphthalene-2-sulfonic acid of approximately 1:1. Preferably, the salt is characterized by a PXRD diffractogram comprising peaks, expressed in degrees 2θ (±0.2°), at 5.1°, 6.5° and 13.1°. More preferably, the PXRD diffractogram further comprises at least three peaks, expressed in degrees 2θ (±0.2°), selected from the group consisting of: 4.5°, 9.0°, 10.0°, 11.5°, 13.6°, 16.4°, 17.2°, 20.2° and 24.3°. Most preferably, the PXRD diffractogram further comprises peaks, expressed in degrees 2θ (±0.2°), at 4.5°, 9.0°, 10.0°, 11.5°, 13.6°, 16.4°, 17.2°, 20.2° and 24.3°.

In another preferred embodiment of the first aspect, the salt is a maleate salt of remdesivir. Preferably, the salt is characterized by a PXRD diffractogram comprising peaks, expressed in degrees 2θ (±0.2°), at 4.6°, 9.0°, and 16.3°. More preferably, the PXRD diffractogram further comprises at least one peak, expressed in degrees 2θ (±) °, selected from the group consisting of: 6.2° and 7.3°. Most preferably, the PXRD diffractogram further comprises peaks, expressed in degrees 2θ (±0.2°), at 6.2° and 7.3°.

In another preferred embodiment of the first aspect, the salt is an oxalate salt of remdesivir. Preferably, the salt is characterized by a PXRD diffractogram comprising peaks, expressed in degrees 2θ (±0.2°), at 7.4°, 10.3° and 22.9°. More preferably, the PXRD diffractogram further comprises at least three peaks, expressed in degrees 2θ (±) 0.2°, selected from the group consisting of: 9.7°, 11.4°, 12.1°, 17.1°, 18.6°, 20.2° and 21.7°. Most preferably, the PXRD diffractogram further comprises peaks, expressed in degrees 2θ (±0.2°), at 9.7°, 11.4°, 12.1°, 17.1°, 18.6°, 20.2° and 21.7°.

In a second aspect of the present invention, there is provided the use of a rotary apparatus in the process of the first aspect, wherein the mixing is conducted in the rotary apparatus by means of rotation of a vessel containing the active pharmaceutical ingredient and the entity about its own axis. Preferably, the vessel has a shape that is selected from the group consisting of a cylindrical shape, a spherical shape, a cubic shape, a double-cone shape, a v-shape, a y-shape, and a diamond-shape. In a further preferred embodiment of the second aspect, the rotary apparatus comprises: a fixed support structure; a vessel rotatably supported about an axis by the fixed support structure and defining a chamber for mixing of the active pharmaceutical ingredient and the entity; an aperture in the vessel enabling communication between the chamber and a source of solvent vapour; and means for rotating the vessel about the axis. In a further preferred embodiment of the second aspect, the vessel is a double-cone shape, formed from the connection of two frusta across their major bases with the interception of a circular cylindrical connector.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

FIG. 6 is a representative PXRD diffractogram of ibrutinib Form APO-V.

FIG. 9 is a representative PXRD diffractogram of lumacaftor Form APO-I.

DESCRIPTION OF THE INVENTION

Figure 1:
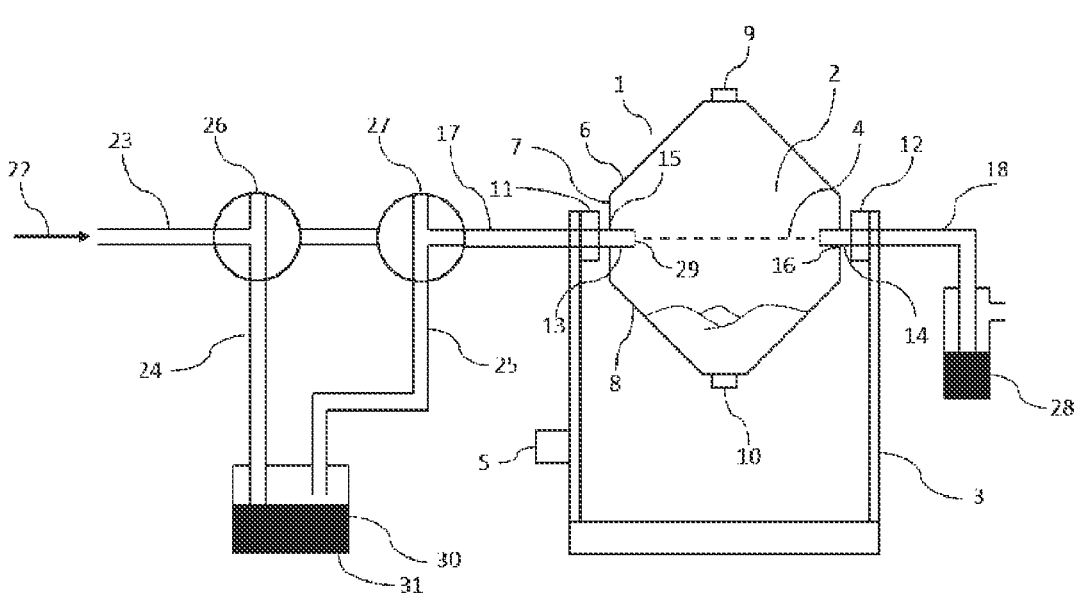
FIG. 1 provides a schematic of a rotary apparatus used in the processes of the present invention, as exemplified in Example 2.

The present invention provides improved processes for the preparation of an existing crystalline solid form of an active pharmaceutical ingredient comprising mixing, in the presence of solvent vapour, of a solid active pharmaceutical ingredient and a pharmaceutically acceptable entity that is either a high-boiling liquid or a solid. Unlike known solvent-based crystalline form preparative methods, the processes of the present invention employ only solvent vapour, resulting in reduced environmental impact including conservation of natural resources and avoidance of pollution.

Lower utilization of solvent in the processes of the invention also results in cost-savings in the form of reduced material costs and reduced solvent waste disposal charges. Further, there are labour cost-savings associated with process simplification since the processes of the present invention eliminate the need for discrete separation and drying operations associated with solvent-based crystalline form preparation methods. Also, the processes of the present invention are simple and can be conducted in standard production equipment commonly employed in the pharmaceutical industry, such as a rotary cone dryer.

Additionally, the processes of the present invention provide health and safety advantages due to the reduced requirement to store and handle large quantities of solvent, which are often flammable, thus lowering exposure and fire risk.

In addition, the use of solvent vapour rather than liquid solvent affords crystalline forms having low levels of residual solvent, which is critical to the regulatory acceptability of APIs, as governed by the ICH (International Council for Harmonisation of Technical Requirements for Pharmaceuticals for Human Use).

As used herein, the term 'crystalline solid form' refers to a solid substance that is in a crystalline state. As used herein, the term 'crystalline solid form' is intended to include salts and multiple-component crystalline forms of an API.

As used herein, the term 'crystalline form' refers to a substance with a particular arrangement of molecular components in its crystal lattice, and which may be identified by physical characterization methods such as PXRD. As used herein, the term 'crystalline form' is intended to include single-component and multiple-component crystalline forms of an API. Single-component forms of an API consist solely of the API in the repeating unit of the crystal lattice. Multiple-component forms of an API, such as the crystalline forms of the present invention, include crystalline forms of an API wherein one or more other coformer molecules are also incorporated into the crystal lattice with the API, and which are not salts.

As used herein, the term 'cocrystal' refers to a multiple-component crystalline form containing both an API and a coformer wherein the coformer is a solid under ambient conditions.

As used herein, the term 'high-boiling liquid' refers to a substance that is a liquid under ambient conditions having a boiling point greater than 150° C. Examples of high-boiling liquids include propylene glycol and methyl benzoate.

As used herein, the term 'coformer' refers to a substance that is incorporated into the crystal lattice with the API in a multiple-component crystalline form of the present invention and which has a melting point greater than approximately 30° C. or a boiling point greater than approximately 150° C. A coformer may itself be an API.

Multi-component crystalline forms comprising more than one type of molecule, such as cocrystals and solvates, may have some variability in the exact molar ratio of their components depending on a variety of conditions used. For example, a molar ratio of components within a multi-component crystalline form provides a person of skill in the art information as to the general relative quantities of the components of the crystalline form. In many cases, the molar ratio may vary by ±20% from a stated range. For example, with respect to the present invention, a molar ratio of 1:1 should be understood to include the ratios 1:0.8 and 1:1.2, as well as all of the individual ratios in between.

As used herein, the term "room temperature" refers to a temperature in the range of 20° C. to 25° C.

As used herein, the term "ambient conditions" refers to surrounding conditions of approximately one atmosphere of pressure, at approximately 50% relative humidity, and at approximately room temperature.

As used herein, the term "frusta" is the plural form of "frustum", which refers to the shape of part of a vessel of the present invention that lies between the base of a cone and a plane cut parallel to it.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

Depending on the manner in which the embodiments of the invention are prepared, the methodology and instrument used for PXRD analysis, the intensity of a given peak observed in a PXRD diffractogram of a crystalline form may vary when compared to the same peak in the representative PXRD diffractograms provided in FIGS. 3 to 13. Thus, differences in relative peak intensities between peaks in a PXRD diffractogram for a given crystalline form may be observed when compared to the relative peak intensities of the peaks in the representative PXRD diffractograms of FIGS. 3 to 13. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIGS. 3 to 13, it is understood that individual peak positions may vary between ±0.2° 2θ from the values observed in the representative PXRD diffractograms provided in FIGS. 3 to 13 for the crystalline forms of the invention, or listed in Tables 1 to 11. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 3 to 13. Thus, PXRD diffractograms of the crystalline forms of the present invention may, in some circumstances, display the same relative peak positions as observed in the representative PXRD diffractograms provided in FIGS. 3 to 13, with the exception that each peak is offset in the same direction, and by approximately the same amount, such that the overall PXRD diffractogram is substantially the same in appearance as a PXRD diffractogram of FIGS. 3 to 13, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 3 to 13.

In one embodiment of the present invention, there is provided a process for the preparation of an existing crystalline solid form comprising an active pharmaceutical ingredient and a distinct pharmaceutically acceptable entity, the process comprising mixing, in the presence of solvent vapour, of:

(i) the active pharmaceutical ingredient in solid form; and (ii) the pharmaceutically acceptable entity, in solid or liquid form, wherein the entity has a melting point greater than approximately 30° C. or a boiling point greater than approximately 150° C. and the pharmaceutically acceptable entity and active pharmaceutical ingredient are incorporated in the same crystalline lattice.

Existing crystalline solid forms of active pharmaceutical ingredients suitable for use in the present invention may be found in, for example, the Cambridge Structural Database (CSD), WO 2019/041026 A1, U.S. Pat. Nos. 10,183,024 B2, 10,513,500 B2, US 2019/112299 A1, US 2019/0343815 A1, or in the general literature available to one skilled in the art. Additionally, existing crystalline solid forms of active pharmaceutical ingredients for use in the present invention include any form, the existence of which has been confirmed prior to applying the processes of the present invention. For example, a crystalline solid form resulting from a solvent-based method may be a suitable target for the processes of the present invention.

The API for use in the present invention is any suitable substance having the requisite pharmacological activity that is a solid at room temperature. Preferably, the API is a free-flowing solid.

In a preferred embodiment, the entity is a coformer and the crystalline solid form is a multiple-component crystalline form, preferably a cocrystal. In this embodiment, the input API may be a neutral compound or a salt thereof. Preferred examples of APIs include acalabrutinib, lesinurad, tetrabenazine, deutetrabenazine, lumacaftor, and ibrutinib. The coformer is any suitable pharmaceutically acceptable substance that is incorporated into the crystal structure with the API in a multiple-component crystalline form of the present invention and which is either a solid at room temperature or which is a high-boiling liquid. The coformer itself may be an API. Preferred examples of coformers include nicotinamide and urea. In addition to an API and a coformer, the multiple-component crystalline forms of the present invention may incorporate one or more other substances, such as an organic solvent or water.

In another embodiment, the entity is an acid or a base and the crystalline solid form is a salt arising from the exchange of a proton between the API and the acid or base. In this embodiment, the input API is a neutral compound comprising either a basic moiety or an acidic moiety to react with the acid or base entity, respectively. Preferably, the API has a basic moiety and the entity is an acid. The basic moiety is preferably a primary, secondary, or tertiary amine bearing substituent(s) which are alkyl, aryl, or both. Secondary and tertiary amines include cyclic and acyclic members, for example secondary and tertiary piperidine and piperazine moieties. Preferred amine moieties include anilines, piperidines, piperazines, and tertiary alkyl amines. Most preferably, the API is remdesivir.

The acid or base is any suitable pharmaceutically acceptable substance that is capable of ionizing the API and which is incorporated into the crystal structure with the API (as the corresponding counterion) and which is either a solid at room temperature or which is a high-boiling liquid. The acid or base itself may be an API. Preferred examples of acids and bases are described in, for example, P. Heinrich Stahl, Camille G. Wermuth (Eds.), *Handbook of Pharmaceutical Salts Properties, Selection, and Use;* 2002. Preferably, the base is selected from the group consisting of sodium hydroxide, calcium hydroxide, potassium hydroxide, magnesium hydroxide, and L-arginine. Preferably, the acid is selected from the group consisting of fumaric acid, maleic acid, L-malic acid, succinic acid, citric acid, L-tartaric acid, oxalic acid, and naphthalene-2-sulfonic acid. In addition to an ionized API and counterion, the salts of the present invention may incorporate one or more other substances, such as an organic solvent or water.

The neat API and entity are mixed together in the presence of solvent vapour. As such, the processes of the present invention are substantially solvent-free in that a liquid solvent is not used as a medium for the formation of the crystalline solid form. The mixing is conducted in the presence of solvent vapour in the absence of liquid solvent. The solvent vapour may arise from any suitable solvent having a sufficient vapour pressure under ambient conditions. Preferably, the suitable solvent has a vapour pressure at room temperature of between approximately 2 kPa and approximately 80 kPa, more preferably it is between approximately 10 kPa and approximately 40 kPa. More preferably, the suitable solvent is selected from the group consisting of ketones, alcohols, and esters. Even more preferably, the suitable solvent is selected from the group consisting of acetone, ethyl acetate, ethanol, and methanol. Most preferably, the suitable solvent is acetone.

Mixing of the API and the entity may be accomplished by any suitable method. Preferably, the mixing of the API and the entity is low-shear mixing. Low-shear mixing is characterized by blending or stirring of a solid(s) without strong energetic transfer and without significantly reducing the particle size. For example, in the processes of the present invention, the volume mean diameter D[4,3] of the particles are reduced by less than approximately 10%, less than approximately 20%, less than approximately 30%, or less than approximately 40% during the mixing process. Low-shear mixers suitable for use in the present invention may combine the API and entity by diffusion or by convection. Diffusion mixing involves repeatedly tilting the components of a mixture such that gravitational forces causes the relative positions of the components to change. Convection mixing involves forceful transfer of portions of the mixture from one location to another by means of an agitator device such as a screw, blade, ribbon, or paddle.

Mixing of the API and the entity may be conducted in a stationary apparatus wherein the components are mixed convectively in a stationary vessel by an agitator device. The stationary vessel defines a chamber for mixing the API and the entity and may have any shape, size, dimension, and construction material suitable for use in pharmaceutical application. Preferably, the shape of the vessel is selected from conical shape, cylindrical shape, and spherical shape. The vessel is typically suspended from the floor by a fixed support structure. The vessel enables loading and unloading of material in any suitable manner such as through one or more ports that are sealable to be made airtight. The vessel bears one or more apertures enabling communication between the chamber and a source of solvent vapour. The vessel may bear one aperture that functions as an inlet for delivery of solvent vapour and one aperture that functions as an outlet for evacuation of solvent vapour. Alternatively, one aperture can operate as both inlet and outlet for solvent vapour in an intermittent fashion. The agitator device may be any element or combination of elements which is suitable for mixing or blending powders and that is operable inside of the chamber where the API and entity reside. The agitator device may comprise a drive means, a shaft, and an impeller. Examples of typical agitator devices used in the pharmaceutical industry for mixing and blending powders include a screw, blade, ribbon, or paddle. The agitator device may be operated by means of a motor, gear reducer, belt system, or other suitable drive means.

An example of a suitable stationary apparatus is a conical screw mixer or dryer. In this type of mixer or dryer, the agitator device is a rotating free-hanging, cantilevered screw suspended from an orbital arm which orbits along the inner periphery of a stationary cone-shaped vessel containing the API and the entity.

Another example of a suitable stationary apparatus is a conical ribbon mixer or dryer. In this type of mixer or dryer, the agitator device is a single or double helical mixing blade mounted from the top of a stationary cone-shaped vessel containing the API and the entity.

Figure 2:
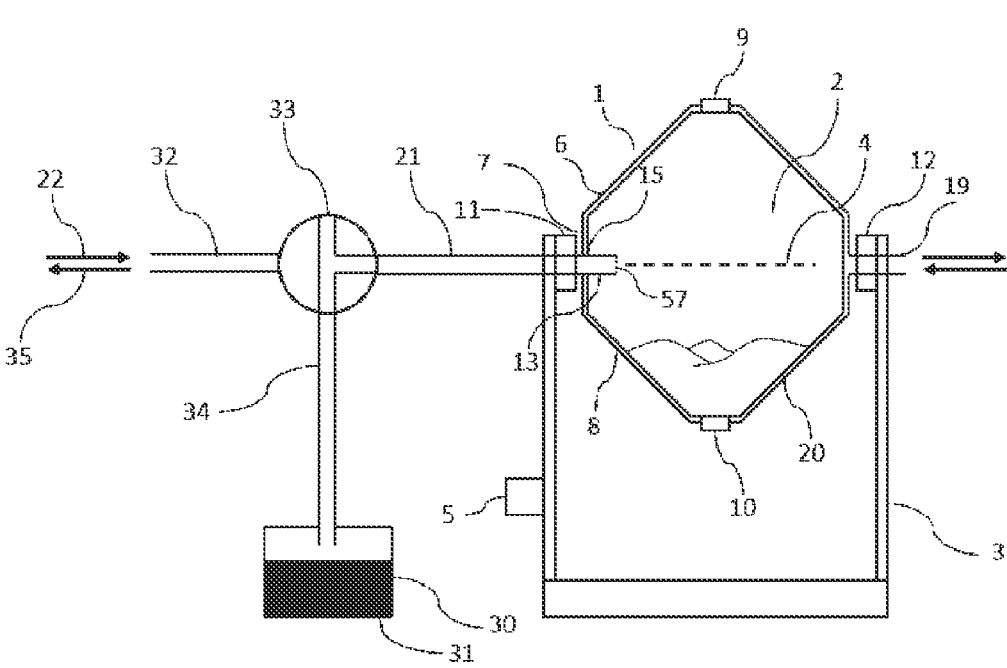
FIG. 2 provides a schematic of an alternative rotary apparatus for use in the processes of the present invention.

In preferred embodiments of the present invention, the process is executed in a rotary apparatus having a configuration such as that shown in FIG. 1 or FIG. 2. In these embodiments, which can be referred to as 'vapour-assisted tumbling', abbreviated 'VAT', the components are mixed diffusively by means of rotation of a vessel 1 about its own axis. The vessel is rotatably supported by a fixed support structure 3, preferably about a substantially horizontal axis 4. The vessel 1 is equipped or adapted to enable introduction and evacuation of solvent vapour such as by the use of a vapour treatment system. The rotation of the vessel 1 is powered by a motor 5, gear reducer, belt system or other suitable drive means.

The vessel 1 defines a chamber 2 for mixing the API and the entity and may be any rotatable vessel having a shape, size, dimensions, and construction material suitable for use in pharmaceutical application. In FIGS. 1 and 2, vessel 1 is double-cone shaped wherein two conical frusta 6 and 8 are joined base to base with a cylindrical connector 7 in between. Preferably, the shape of the vessel 1 is selected from the group consisting of cylindrical shape, spherical shape, cubic shape, double-cone shape, v-shape, y-shape, and diamond-shape. The vessel 1 enables loading and unloading of material in any suitable manner such as through one or more ports that are sealable to be made airtight. In FIGS. 1 and 2, vessel 1 bears a loading port 9 at the top for loading the API and the entity and a discharge port 10 at the bottom for discharging the product.

The vessel 1 is rotatably connected to the fixed support structure 3. In FIG. 1, the vessel 1 is supported by the fixed support structure 3 through two bearings 11 and 12. Each bearing 11 and 12 rotatably supports a respective hollow shaft 13 and 14 that is coaxial with the rotation axis 4 and communicates with the chamber 2 through respective apertures 15 and 16. The hollow shafts 13 and 14 communicate with respective lines 17 and 18 through which solvent vapour is respectively delivered and evacuated during the process. Alternatively, as shown in FIG. 2, the vessel 1 is supported by the fixed support structure 3 through two bearings 11 and 12. Each bearing 11 and 12 rotatably supports a respective hollow shaft 13 and 19 that is coaxial with the rotation axis 4. Hollow shaft 13 communicates with the chamber 2 through aperture 15 whereas hollow shaft 19 may communicate with an interspace 20 formed between two walls of the vessel 1 for carrying heating fluid. The hollow shaft 13 communicates with a line 21 to successively introduce and evacuate solvent vapour from the vessel 1.

The requisite solvent vapour may be generated by a vapour treatment system. In the vapour treatment system shown in FIG. 1, an inert gas such as nitrogen 22 is passed via line 23 through a first three-way valve 26, which aligns line 23 with line 24, into a solvent reservoir 30 containing liquid solvent 31 to generate a flow of solvent vapour. Line 25, positioned in the headspace of solvent reservoir 30, carries the resulting solvent vapour through a second three-way valve 27 that aligns line 25 and line 17 and into the chamber 2. The vapour fills the chamber and exits through line 18. The spent vapour can be routed through a back-flow prevention device, shown in FIG. 1 as a bubbler 28 that is filled with an inert oil. In the system shown in FIG. 1, solvent vapour is continuously delivered to the chamber throughout the mixing process. The system may also be operated in other modes, such as intermittently. An alternative vapour treatment system is shown in FIG. 2, wherein chamber 2 is first evacuated by aligning line 32 and line 21 via three-way valve 33 and applying vacuum 35 to the line. Solvent vapour is then introduced into the chamber 2 from the headspace of solvent reservoir 30 by turning valve 33 to align line 34 and line 21. In this embodiment, the solvent vapour fills the chamber 2 by equilibration.

Preferably, the vessel 1 is rotated at a speed of between approximately 5 rpm and approximately 40 rpm, more preferably between approximately 20 rpm and approximately 30 rpm. The mixing may be conducted at any suitable temperature, preferably the temperature is in the range of from approximately 15° C. to approximately ° C. Most preferably, the mixing is conducted at room temperature.

During the mixing process, lumps or agglomerates that form may be dispersed or broken apart by a lump breaker or de-lumper positioned inside of the chamber.

An example of a suitable industrial rotary apparatus is a rotary cone mixer or dryer which is configured and operated in a manner similar to the embodiments shown in FIG. 1 or FIG. 2.

Further standard parts and accessories of mixing apparatuses for use in the present invention, such as valves, hoses, loading/discharge ports, bearings, seals, and heating/cooling jackets are peripheral components and a variety of suitable configurations are known to a person of skill in the art.

In another embodiment of the present invention, the processes provide a multiple component crystalline form that is a cocrystal of an active pharmaceutical ingredient and nicotinamide. Preferred examples of the active pharmaceutical ingredient of the nicotinamide cocrystal are selected from the group consisting of celecoxib, nebivolol hydrochloride, carbazepine, ibuprofen, apremilast, flufenamic acid, acyclovir, adefovir dipivoxil, olanzapine, 5-fluorouracil, acetacin, theophylline, febuxostat, isoniazid, diflunisal, ticagrelor, artesunate, prulifloxacin, tegafur, baicalein, lesinurad, acalabrutinib, and lumacaftor. Most preferably, the active pharmaceutical ingredient is selected from the group consisting of acalabrutinib, lesinurad, and lumacaftor.

In another embodiment of the present invention, the processes provide a multiple component crystalline form that is a cocrystal of acalabrutinib with a coformer having a melting point greater than approximately 30° C. Preferred examples of acalabrutinib cocrystals are described in WO 2019/041026 A1 including acalabrutinib urea cocrystal, acalabrutinib nicotinamide cocrystal, and acalabrutinib L-sorbitol cocrystal.

In another embodiment of the present invention, the processes provide a cocrystal of acalabrutinib and nicotinamide. Preferably, in the cocrystal of acalabrutinib and nicotinamide, the molar ratio of acalabrutinib to nicotinamide is approximately 1:2. More preferably, the cocrystal of acalabrutinib and nicotinamide is Form APO-II.

Acalabrutinib Form APO-II can be characterized by a PXRD diffractogram comprising, among other peaks, characteristic peaks, expressed in degrees 2θ (±0.2°), at 5.8°, 7.2° and 14.6°. Preferably, the PXRD diffractogram further comprises at least three peaks, expressed in degrees 2θ (±0.2°), selected from the group consisting of 9.2°, 11.4°, 12.8°, 16.0°, 18.5°, 21.1°, 21.9°, 23.4° and 24.1°. More preferably, the PXRD diffractogram further comprises peaks, expressed in degrees 2θ (±0.2°), at 9.2°, 11.4°, 12.8°, 16.0°, 18.5°, 21.1°, 21.9°, 23.4° and 24.1°.

Figure 3:
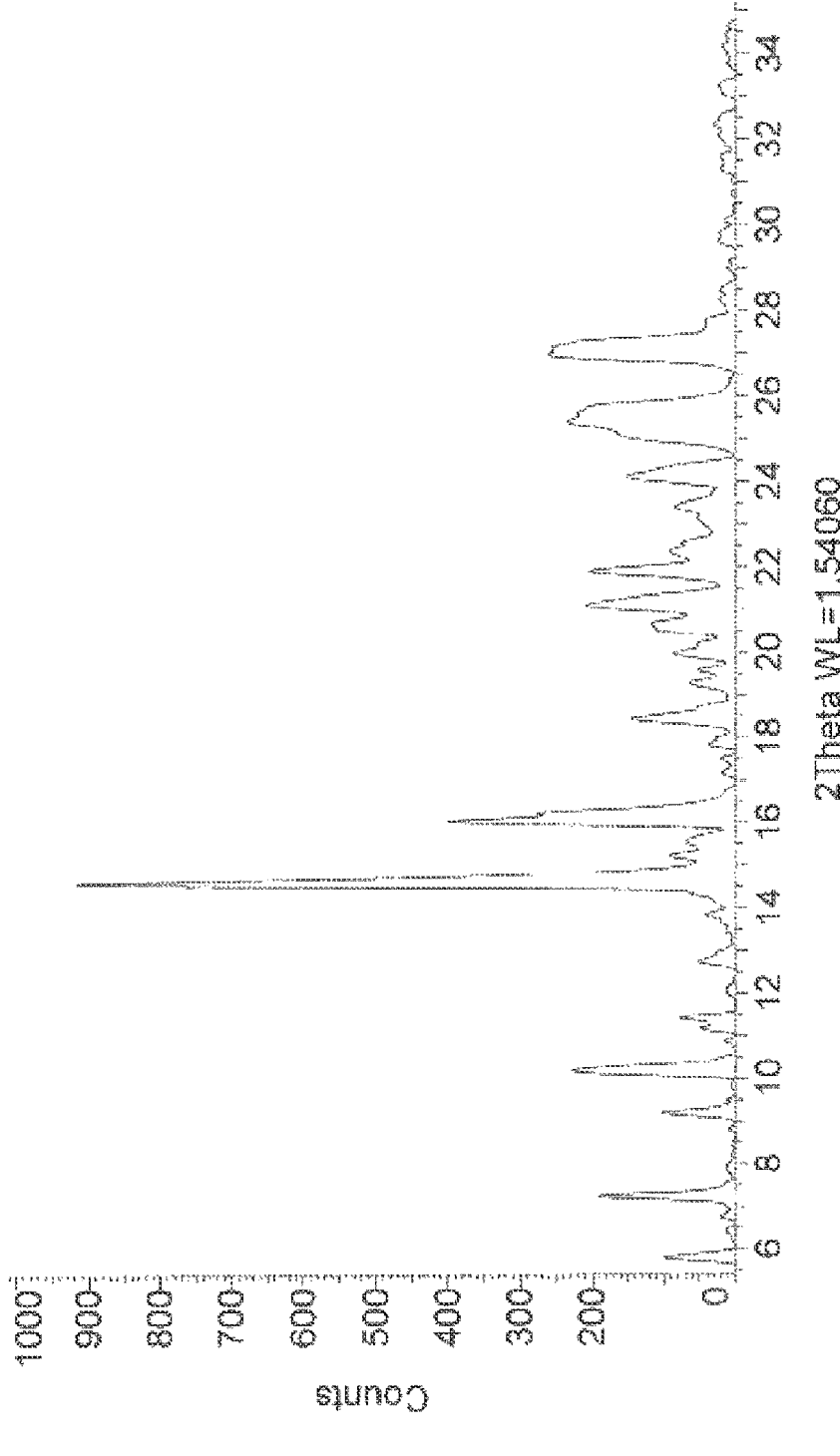
FIG. 3 is a representative PXRD diffractogram of acalabrutinib Form APO-II.

An illustrative PXRD diffractogram of acalabrutinib Form APO-II is shown in FIG. 3. A peak listing, comprising representative peaks from the PXRD diffractogram in FIG. 3, and their relative intensities, is provided in Table 1. Although illustrative of the PXRD diffractogram that is provided for the acalabrutinib Form APO-II of the present invention, the relative intensities of the peaks are variable. Thus, depending on a particular sample, the prominence or relative intensity of the peaks observed may differ from those in the illustrative PXRD diffractogram and peak listing.

TABLE 1

| Relative peak intensities of acalabrutinib Form APO-II from FIG. 3 | |
| --- | --- |
| Angle (° 2θ) | Relative intensity (%) |
| 5.80 | 7.2 |
| 7.24 | 17.9 |
| 9.20 | 8.7 |
| 10.20 | 17.4 |
| 11.42 | 6.0 |
| 12.78 | 4.6 |
| 14.59 | 100.0 |
| 16.02 | 43.0 |
| 16.24 | 29.6 |
| 18.47 | 11.9 |
| 19.99 | 6.2 |
| 20.65 | 9.9 |
| 21.13 | 20.3 |
| 21.90 | 18.1 |
| 23.43 | 7.3 |
| 24.12 | 15.0 |
| 25.59 | 23.3 |
| 27.04 | 26.9 |

In another embodiment of the present invention, the processes of the present invention provide a cocrystal of acalabrutinib and urea. Preferably, in the cocrystal of acalabrutinib and urea, the molar ratio of acalabrutinib to urea is approximately 1:2. More preferably, the cocrystal of acalabrutinib and urea is Form APO-V.

Acalabrutinib Form APO-V can be characterized by a PXRD diffractogram comprising, among other peaks, characteristic peaks, expressed in degrees 2θ (±0.2°), at 5.4°, 6.6° and 11.0°. Preferably, the PXRD diffractogram further comprises at least three peaks, expressed in degrees 2θ (±0.2°), selected from the group consisting of 13.2°, 15.1°, 17.3°, 19.9°, 21.1° and 22.2°. More preferably, the PXRD diffractogram further comprises peaks, expressed in degrees 2θ (±0.2°), at 10.1°, 13.2°, 17.3°, 19.9°, 21.1° and 22.2°.

Figure 4:
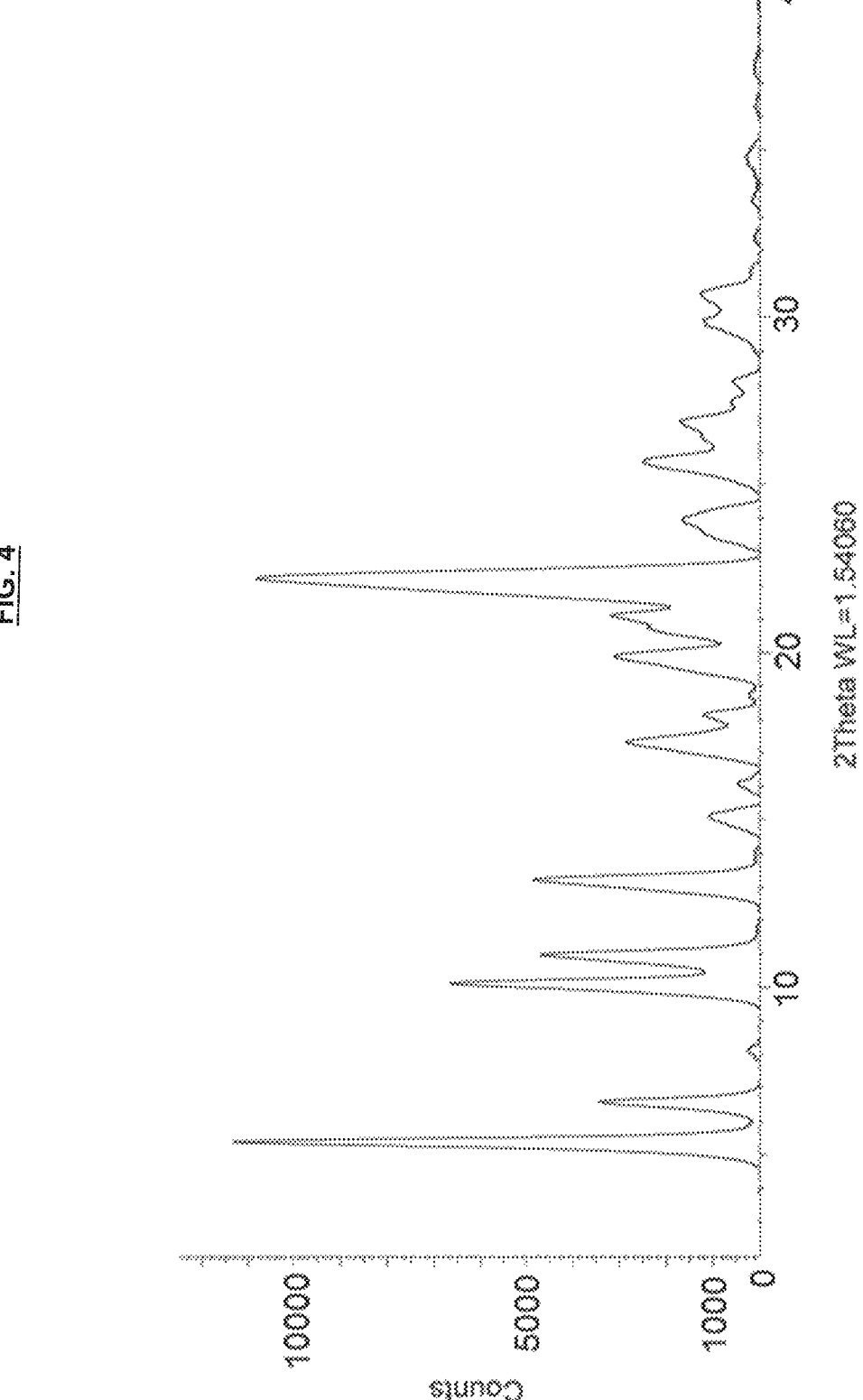
FIG. 4 is a representative PXRD diffractogram of acalabrutinib Form APO-V.

An illustrative PXRD diffractogram of acalabrutinib Form APO-V is shown in FIG. 4. A peak listing, comprising representative peaks from the PXRD diffractogram in FIG. 4, and their relative intensities, is provided in Table 2. Although illustrative of the PXRD diffractogram that is provided for the acalabrutinib Form APO-V of the present invention, the relative intensities of the peaks are variable. Thus, depending on a particular sample, the prominence or relative intensity of the peaks observed may differ from those in the illustrative PXRD diffractogram and peak listing.

TABLE 2

Relative peak intensities of acalabrutinib Form APO-V from FIG. 4

| Angle (° 2θ) | Relative intensity (%) |
|---|---|
| 5.38 | 100.0 |
| 6.59 | 30.3 |
| 8.11 | 2.0 |
| 10.12 | 58.7 |
| 10.98 | 41.6 |
| 13.22 | 42.9 |
| 15.12 | 9.6 |
| 16.11 | 4.0 |
| 17.33 | 25.3 |
| 19.90 | 27.5 |
| 21.10 | 28.0 |
| 22.22 | 95.6 |
| 24.01 | 14.6 |
| 25.70 | 22.0 |

In another embodiment of the present invention, the processes provide a solvate of ibrutinib and methyl benzoate. Preferably, in the solvate of ibrutinib and methyl benzoate, the molar ratio of ibrutinib to methyl benzoate is approximately 1:0.5. More preferably, the solvate of ibrutinib and methyl benzoate is Form APO-II.

Ibrutinib Form APO-II can be characterized by a PXRD diffractogram comprising, among other peaks, characteristic peaks, expressed in degrees 2θ (±0.2°), at 6.4°, 10.1° and 12.8°. Preferably, the PXRD diffractogram further comprises at least three peaks, expressed in degrees 2θ (±0.2°), selected from the group consisting of: 13.8°, 17.6°, 18.4°, 19.4°, 20.4°, 21.0°, 21.7°, 23.2°, 24.1° and 24.9°. More preferably, the PXRD diffractogram further comprises peaks, expressed in degrees 2θ (±0.2°), at 13.8°, 17.6°, 18.4°, 19.4°, 20.4°, 21.0°, 21.7°, 23.2°, 24.1° and 24.9°.

Figure 5:
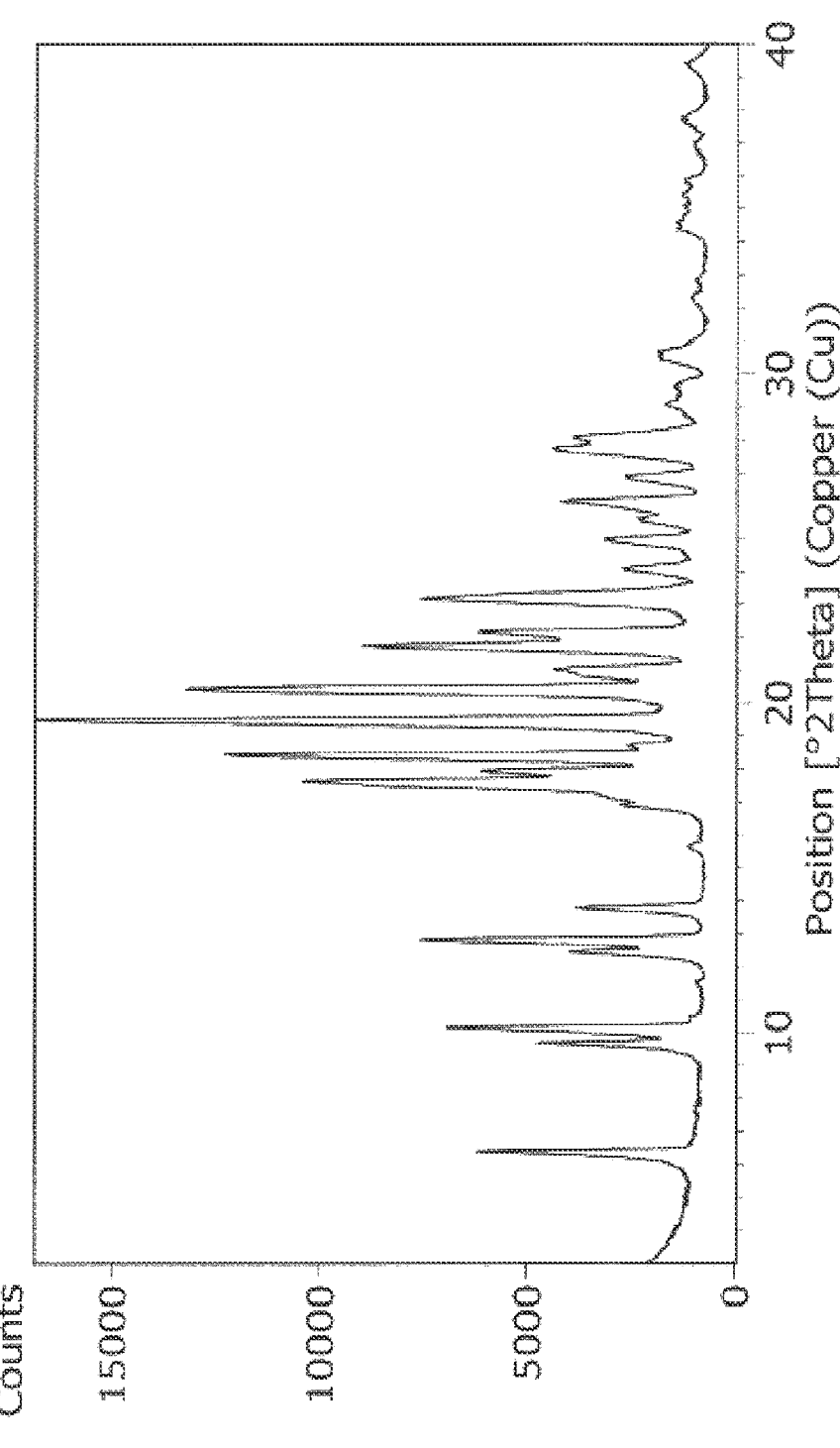
FIG. 5 is a representative PXRD diffractogram of ibrutinib Form APO-II.

An illustrative PXRD diffractogram of ibrutinib Form APO-II is shown in FIG. 5. A peak listing, comprising representative peaks from the PXRD diffractogram in FIG. 5, and their relative intensities, is provided in Table 3. Although illustrative of the PXRD diffractogram that is provided for the ibrutinib Form APO-II of the present invention, the relative intensities of the peaks are variable. Thus, depending on a particular sample, the position and prominence or relative intensity of the peaks observed may differ from those in the illustrative PXRD diffractogram and peak listing.

TABLE 3

Relative peak intensities of ibrutinib Form APO-II from FIG. 5

| Angle (° 2θ) | Relative intensity (%) |
|---|---|
| 6.37 | 40.9 |
| 9.66 | 27.9 |
| 10.14 | 47.0 |
| 12.44 | 19.1 |
| 12.79 | 48.9 |
| 13.77 | 23.2 |
| 17.65 | 47.2 |
| 17.94 | 27.0 |
| 18.39 | 70.7 |
| 19.45 | 100.0 |
| 20.40 | 77.7 |
| 21.03 | 22.0 |
| 21.72 | 50.3 |
| 22.13 | 30.2 |
| 23.15 | 44.4 |
| 24.06 | 11.8 |
| 24.93 | 17.0 |

In another embodiment of the present invention, the processes provide a new crystalline form of ibrutinib, ibrutinib Form APO-V, which is a cocrystal of Ibrutinib and methyl nicotinate. Preferably, in ibrutinib Form APO-V, the molar ratio of Ibrutinib to methyl nicotinate is approximately 1:0.5.

Ibrutinib Form APO-V can be characterized by a PXRD diffractogram comprising, among other peaks, characteristic peaks, expressed in degrees 2θ (±0.2°), at 6.4°, 10.1° and 12.7°. Preferably, the PXRD diffractogram further comprises at least three peaks, expressed in degrees 2θ (±0.2°), selected from the group consisting of: 9.7, 13.7°, 17.5°, 18.3°, 19.4°, 20.3°, 20.8°, 21.6°, 22.0 and 23.1°. More preferably, the PXRD diffractogram further comprises peaks, expressed in degrees 2θ (±0.2°), at 9.7, 13.7°, 17.5°, 18.3°, 19.4°, 20.3°, 20.8°, 21.6°, 22.0 and 23.1°.

An illustrative PXRD diffractogram of ibrutinib Form APO-V is shown in FIG. 6. A peak listing, comprising representative peaks from the PXRD diffractogram in FIG. 6, and their relative intensities, is provided in Table 4. Although illustrative of the PXRD diffractogram that is provided for the ibrutinib Form APO-V of the present invention, the relative intensities of the peaks are variable. Thus, depending on a particular sample, the position and prominence or relative intensity of the peaks observed may differ from those in the illustrative PXRD diffractogram and peak listing.

TABLE 4

Relative peak intensities of ibrutinib Form APO-V from FIG. 6

| Angle (° 2θ) | Relative intensity (%) |
|---|---|
| 6.39 | 22.6 |
| 9.66 | 18.2 |
| 10.12 | 45.1 |
| 12.39 | 21.9 |
| 12.71 | 67.6 |
| 13.67 | 24.2 |
| 17.52 | 57.4 |
| 18.29 | 76.0 |

TABLE 4-continued

Relative peak intensities of ibrutinib Form APO-V from FIG. 6

| Angle (° 2θ) | Relative intensity (%) |
|---|---|
| 19.39 | 100.0 |
| 20.27 | 70.7 |
| 20.84 | 22.5 |
| 21.64 | 41.0 |
| 21.98 | 27.8 |
| 23.11 | 50.2 |

In another embodiment of the present invention, the processes provide a cocrystal of tetrabenazine and quercetin. Preferably, in the cocrystal of tetrabenazine and quercetin, the molar ratio of tetrabenazine to quercetin is approximately 1:1. More preferably, the cocrystal of tetrabenazine and quercetin is Form APO-I.

Tetrabenazine Form APO-I can be characterized by a PXRD diffractogram comprising, among other peaks, characteristic peaks, expressed in degrees 2θ (±0.2°), at 6.3°, 9.4° and 14.3°. Preferably, the PXRD diffractogram further comprises at least three peaks, expressed in degrees 2θ (±0.2°), selected from the group consisting of 7.0°, 11.1°, 12.5°, 15.8° and 18.8°. More preferably, the PXRD diffractogram further comprises peaks, expressed in degrees 2θ (±0.2°), at 7.0°, 10.4°, 11.1°, 12.5°, 15.8° and 18.8°.

Figure 7:
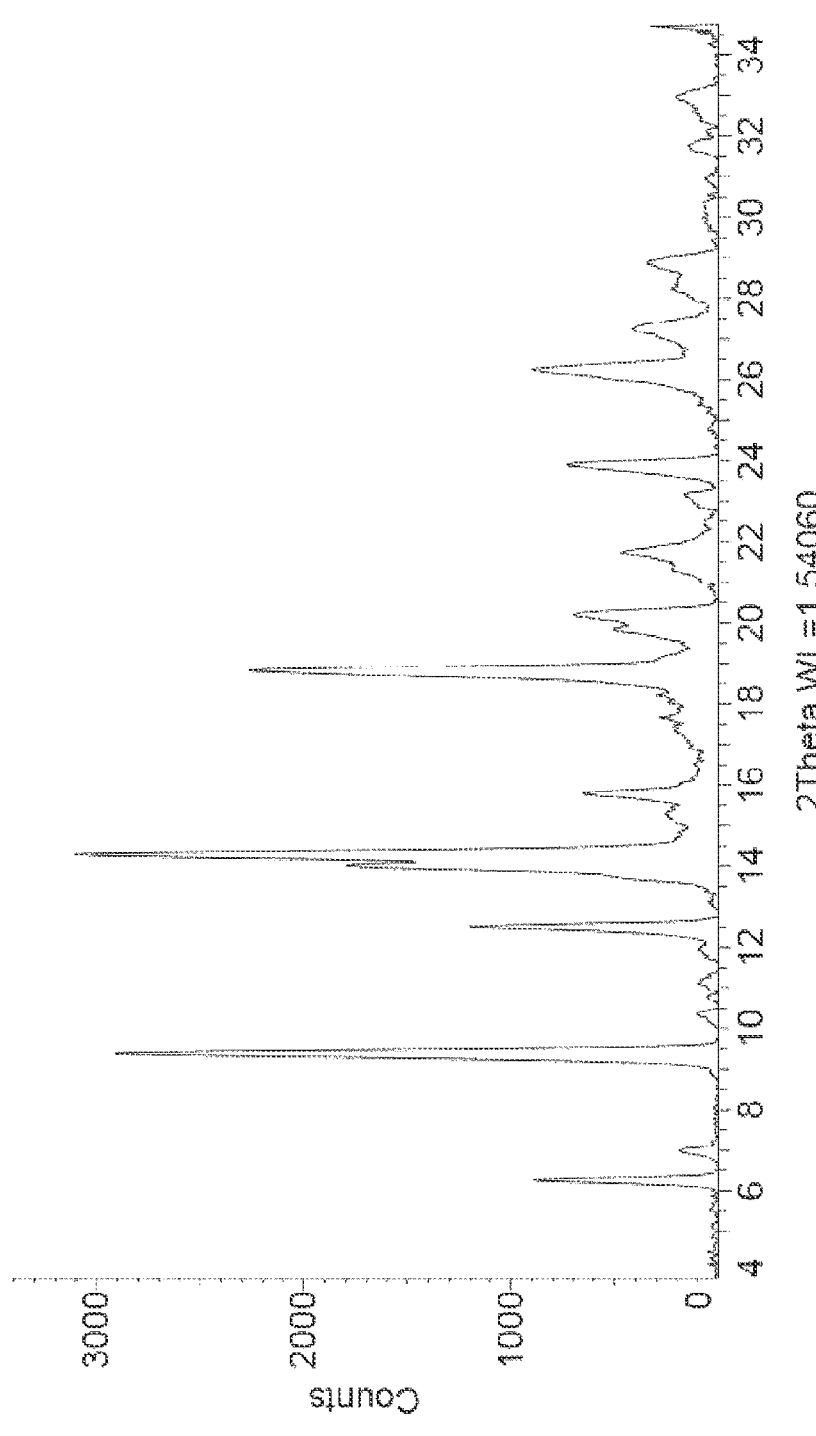
FIG. 7 is a representative PXRD diffractogram of tetrabenazine Form APO-I.

An illustrative PXRD diffractogram of tetrabenazine Form APO-I is shown in FIG. 7. A peak listing, comprising representative peaks from the PXRD diffractogram in FIG. 7, and their relative intensities, is provided in Table 5. Although illustrative of the PXRD diffractogram that is provided for the tetrabenazine Form APO-I of the present invention, the relative intensities of the peaks are variable. Thus, depending on a particular sample, the prominence or relative intensity of the peaks observed may differ from those in the illustrative PXRD diffractogram and peak listing.

TABLE 5

Relative peak intensities of tetrabenazine Form APO-I from FIG. 7

| Angle (° 2θ) | Relative intensity (%) |
|---|---|
| 6.26 | 28.9 |
| 7.00 | 6.0 |
| 9.39 | 93.9 |
| 10.37 | 3.2 |
| 11.12 | 3.2 |
| 12.51 | 38.8 |
| 14.02 | 57.9 |
| 14.30 | 100.0 |
| 15.80 | 21.0 |
| 18.84 | 72.9 |
| 19.83 | 16.2 |
| 20.20 | 22.4 |
| 21.73 | 15.1 |
| 23.90 | 23.5 |
| 26.25 | 29.0 |

In another embodiment of the present invention, the processes provide a cocrystal of lesinurad and nicotinamide. Preferably, in the cocrystal of lesinurad and nicotinamide, the molar ratio of lesinurad to nicotinamide is approximately 1:1. More preferably, the cocrystal of lesinurad and nicotinamide is Form APO-III.

Lesinurad Form APO-III can be characterized by a PXRD diffractogram comprising, among other peaks, characteristic peaks, expressed in degrees 2θ (±0.2°), at 6.2° and 19.9°. Preferably, the PXRD diffractogram further comprises at least four peaks, expressed in degrees 2θ (±0.2°), selected from the group consisting of: 7.6°, 14.1°, 15.3°, 17.8°, 21.1°, 23.4°, 25.7° and 27.2°. More preferably, the PXRD diffractogram further comprises peaks, expressed in degrees 2θ (±0.2°), at 7.6°, 10.3°, 14.1°, 15.3°, 17.8°, 21.1°, 23.4°, 25.7° and 27.2°.

Figure 8:
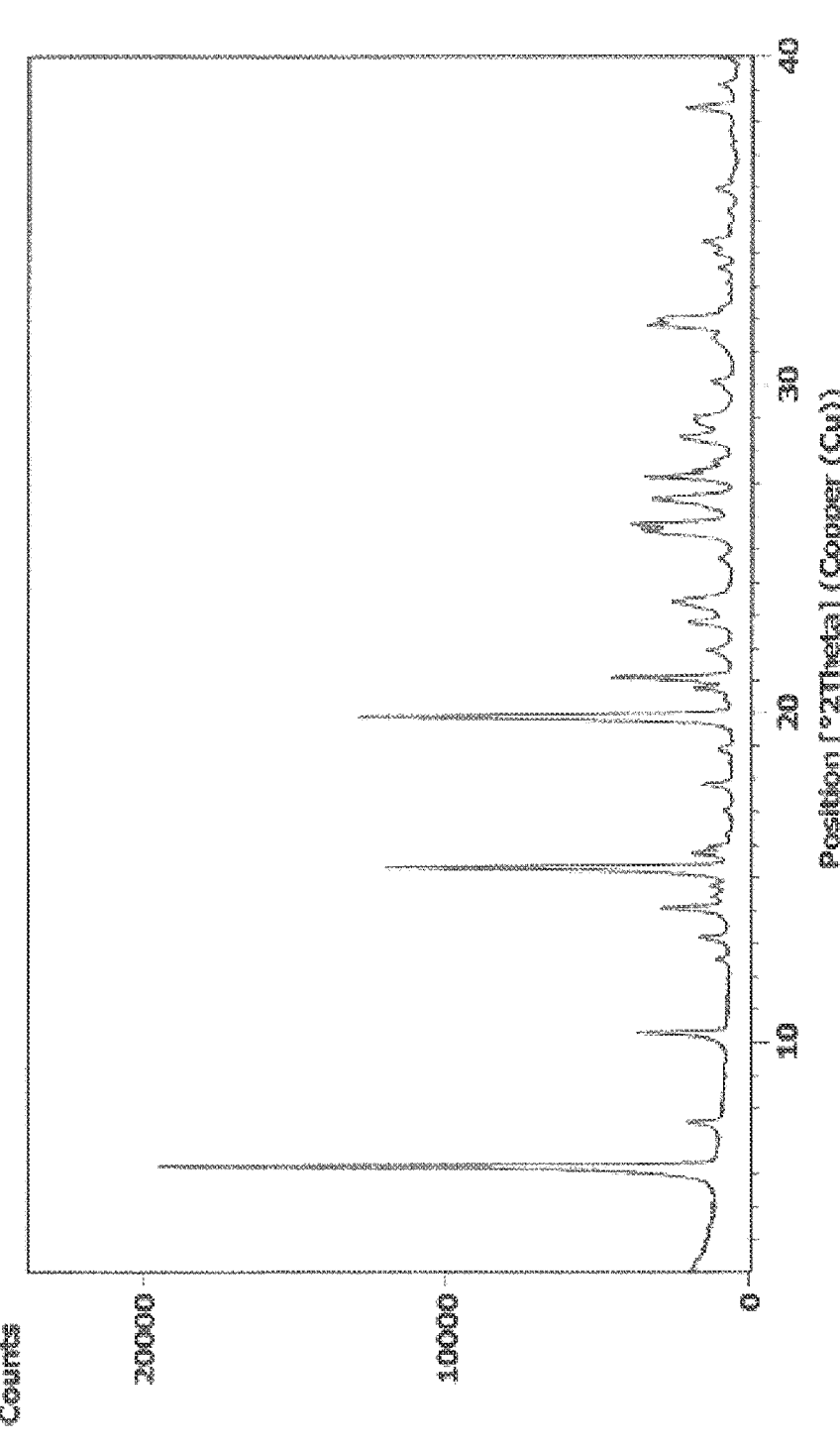
FIG. 8 is a representative PXRD diffractogram of lesinurad Form APO-Ill.

An illustrative PXRD diffractogram of lesinurad Form APO-III is shown in FIG. 8. A peak listing, comprising representative peaks from the PXRD diffractogram in FIG. 8, and their relative intensities, is provided in Table 6. Although illustrative of the PXRD diffractogram that is provided for the lesinurad Form APO-III of the present invention, the relative intensities of the peaks are variable. Thus, depending on a particular sample, the prominence or relative intensity of the peaks observed may differ from those in the illustrative PXRD diffractogram and peak listing.

TABLE 6

Relative peak intensities of lesinurad Form APO-III from FIG. 8

| Angle (° 2θ) | Relative intensity (%) |
|---|---|
| 6.20 | 100.00 |
| 7.55 | 6.84 |
| 10.26 | 18.30 |
| 13.16 | 5.79 |
| 14.05 | 12.57 |
| 14.44 | 2.61 |
| 14.75 | 2.58 |
| 15.28 | 63.71 |
| 15.74 | 6.80 |
| 15.93 | 4.10 |
| 17.82 | 6.29 |
| 19.89 | 70.92 |
| 20.75 | 6.55 |
| 21.07 | 22.84 |
| 21.88 | 4.32 |
| 22.76 | 7.64 |
| 23.38 | 9.42 |
| 25.47 | 10.86 |
| 25.74 | 18.82 |
| 26.52 | 14.22 |
| 27.18 | 16.53 |
| 28.36 | 8.28 |
| 28.97 | 5.58 |

In another embodiment of the present invention, the processes provide a cocrystal of lumacaftor and nicotinamide. Preferably, in the cocrystal of lumacaftor and nicotinamide, the molar ratio of lumacaftor to nicotinamide is approximately 1:2. More preferably, the cocrystal of lumacaftor and nicotinamide is Form APO-I.

Lumacaftor Form APO-I can be characterized by a PXRD diffractogram comprising, among other peaks, characteristic peaks, expressed in degrees 2θ (±0.2°), at 5.7°, 8.5° and 17.0°. Preferably, the PXRD diffractogram further comprises peaks, expressed in degrees 2θ (±0.2°), at 11.3°, 15.4°, 17.8° and 19.8°.

An illustrative PXRD diffractogram of lumacaftor Form APO-I is shown in FIG. 9. A peak listing, comprising representative peaks from the PXRD diffractogram in FIG. 9, and their relative intensities, is provided in Table 7. Although illustrative of the PXRD diffractogram that is provided for the lumacaftor Form APO-I of the present invention, the relative intensities of the peaks are variable. Thus, depending on a particular sample, the prominence or relative intensity of the peaks observed may differ from those in the illustrative PXRD diffractogram and peak listing.

TABLE 7

| Relative peak intensities of lumacaftor Form APO-I from FIG. 9 | |
| Angle (° 2θ) | Relative intensity (%) |
| --- | --- |
| 5.67 | 25.4 |
| 8.47 | 56.2 |
| 11.29 | 4.6 |
| 15.42 | 17.8 |
| 16.95 | 100.0 |
| 17.79 | 10.8 |
| 19.75 | 16.4 |

In another embodiment of the present invention, the processes provide a salt of an active pharmaceutical ingredient and a pharmaceutically acceptable acid. Preferably, the active pharmaceutical ingredient possesses a primary, secondary, or tertiary amine moiety. Preferably, the acid has a melting point greater than approximately ° C. Preferred examples of the acid are selected from the group consisting of fumaric acid, maleic acid, L-malic acid, succinic acid, citric acid, L-tartaric acid, oxalic acid, and naphthalene-2-sulfonic acid. Preferred examples of the salt are selected from the group consisting of tenofovir alafenamide hemifumarate, fesoterodine fumarate, neratinib maleate, remdesivir maleate, sunitinib L-malate, desvenlafaxine succinate, ribociclib succinate, sumatriptan succinate, tofacitinib citrate, sildenafil citrate, zolpidem L-tartrate, rivastigmine L-tartrate, escitalopram oxalate, remdesivir oxalate, and remdesivir napsylate. Most preferably, the salt is selected from the group consisting of remdesivir maleate, remdesivir oxalate, and remdesivir napsylate.

In another embodiment of the present invention, the processes provide a salt of remdesivir, remdesivir napsylate Form APO-I, wherein the molar ratio of remdesivir to naphthalene-2-sulfonic acid is approximately 1:1.

Remdesivir napsylate Form APO-1 can be characterized by a PXRD diffractogram comprising, among other peaks, characteristic peaks, expressed in degrees 2θ (±0.2°), at 5.1°, 6.5° and 13.1°. Preferably, the PXRD diffractogram further comprises at least three peaks, expressed in degrees 2θ (±0.2°), selected from the group consisting of 4.5°, 9.0°, 10.0°, 11.5°, 13.6°, 15.3°, 16.4°, 17.2°, 20.2° and 24.3°. More preferably, the PXRD diffractogram further comprises peaks, expressed in degrees 2θ (±0.2°), at 4.5°, 9.0°, 10.0°, 11.5°, 13.6°, 15.3°, 16.4°, 17.2°, 20.2° and 24.3°.

Figure 10:
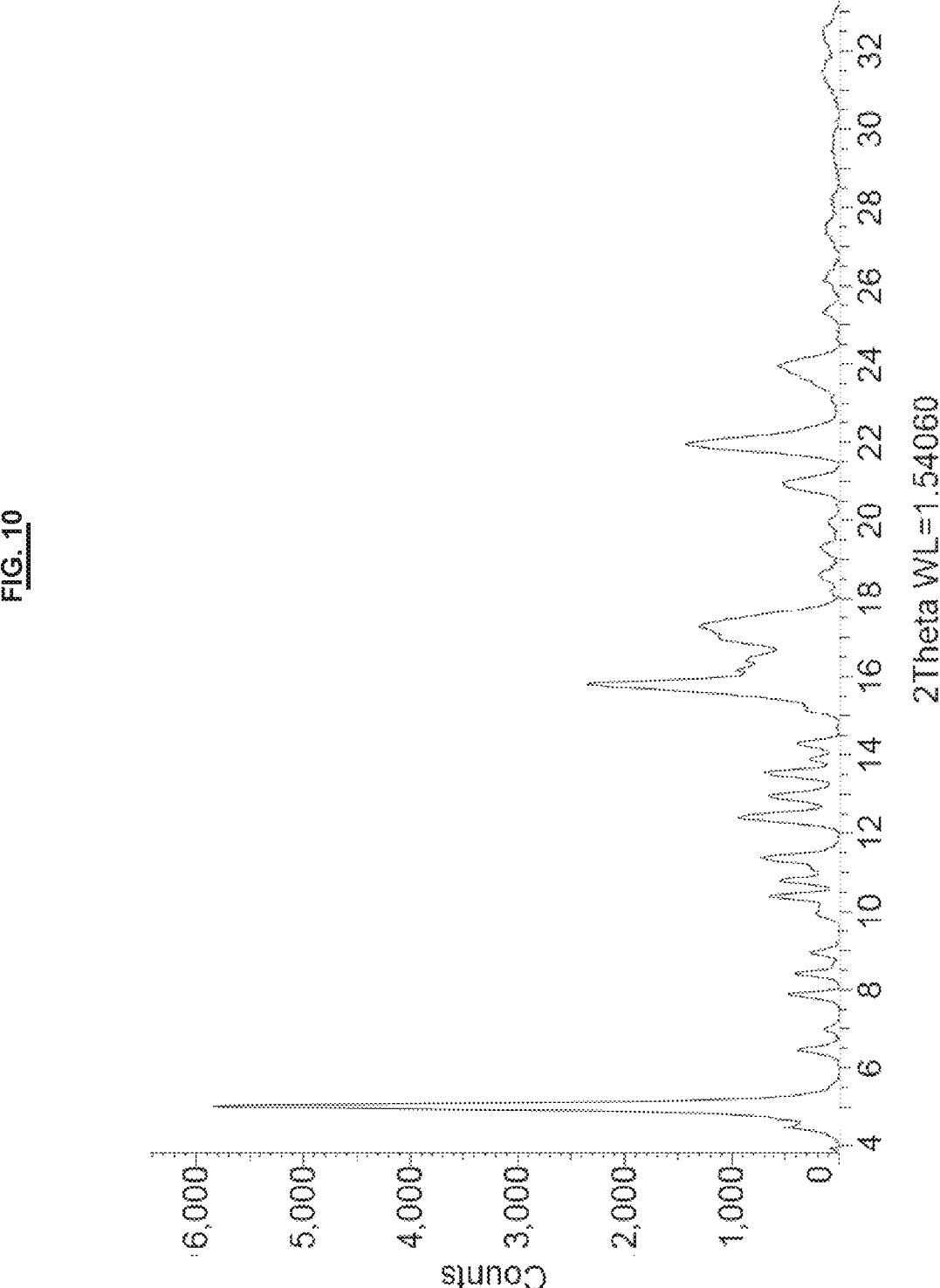
FIG. 10 is a representative PXRD diffractogram of remdesivir napsylate Form APO-I.

An illustrative PXRD diffractogram of remdesivir napsylate Form APO-1, as prepared in Example 8, is shown in FIG. 10. A peak listing, comprising representative peaks from the PXRD diffractogram in FIG. 10, and their relative intensities, is provided in Table 8. Although illustrative of the PXRD diffractogram that is provided for the remdesivir napsylate Form APO-1 of the present invention, the relative intensities of the peaks are variable. Thus, depending on a particular sample, the prominence or relative intensity of the peaks observed may differ from those in the illustrative PXRD diffractogram and peak listing.

TABLE 8

| Relative peak intensities of remdesivir napsylate Form APO-I from FIG. 10 | |
| Angle (2θ) | Relative intensity (%) |
| --- | --- |
| 4.48 | 6.9 |
| 5.08 | 100.0 |
| 6.53 | 9.9 |

TABLE 8-continued

| Relative peak intensities of remdesivir napsylate Form APO-I from FIG. 10 | |
| Angle (2θ) | Relative intensity (%) |
| --- | --- |
| 9.04 | 4.7 |
| 10.03 | 7.2 |
| 11.48 | 18.0 |
| 13.10 | 40.3 |
| 13.60 | 5.8 |
| 15.33 | 11.9 |
| 16.36 | 35.0 |
| 17.20 | 21.3 |
| 20.16 | 8.9 |
| 21.15 | 6.2 |
| 24.25 | 15.1 |

In another embodiment of the present invention, the processes provide a salt of remdesivir, remdesivir maleate Form I as described in WO 2018/204198 A1.

Remdesivir maleate Form I can be characterized by a PXRD diffractogram comprising, among other peaks, characteristic peaks, expressed in degrees 2θ (±0.2°), at 4.6°, 9.0° and 16.3°. Preferably, the PXRD diffractogram further comprises at least three peaks, expressed in degrees 2θ (±0.2°), selected from the group consisting of 6.2°, 7.3°, 14.7°, 15.1° and 17.8°. More preferably, the PXRD diffractogram further comprises peaks, expressed in degrees 2θ (±0.2°), at 6.2°, 7.3°, 14.7°, 15.1° and 17.8°.

Figure 11:
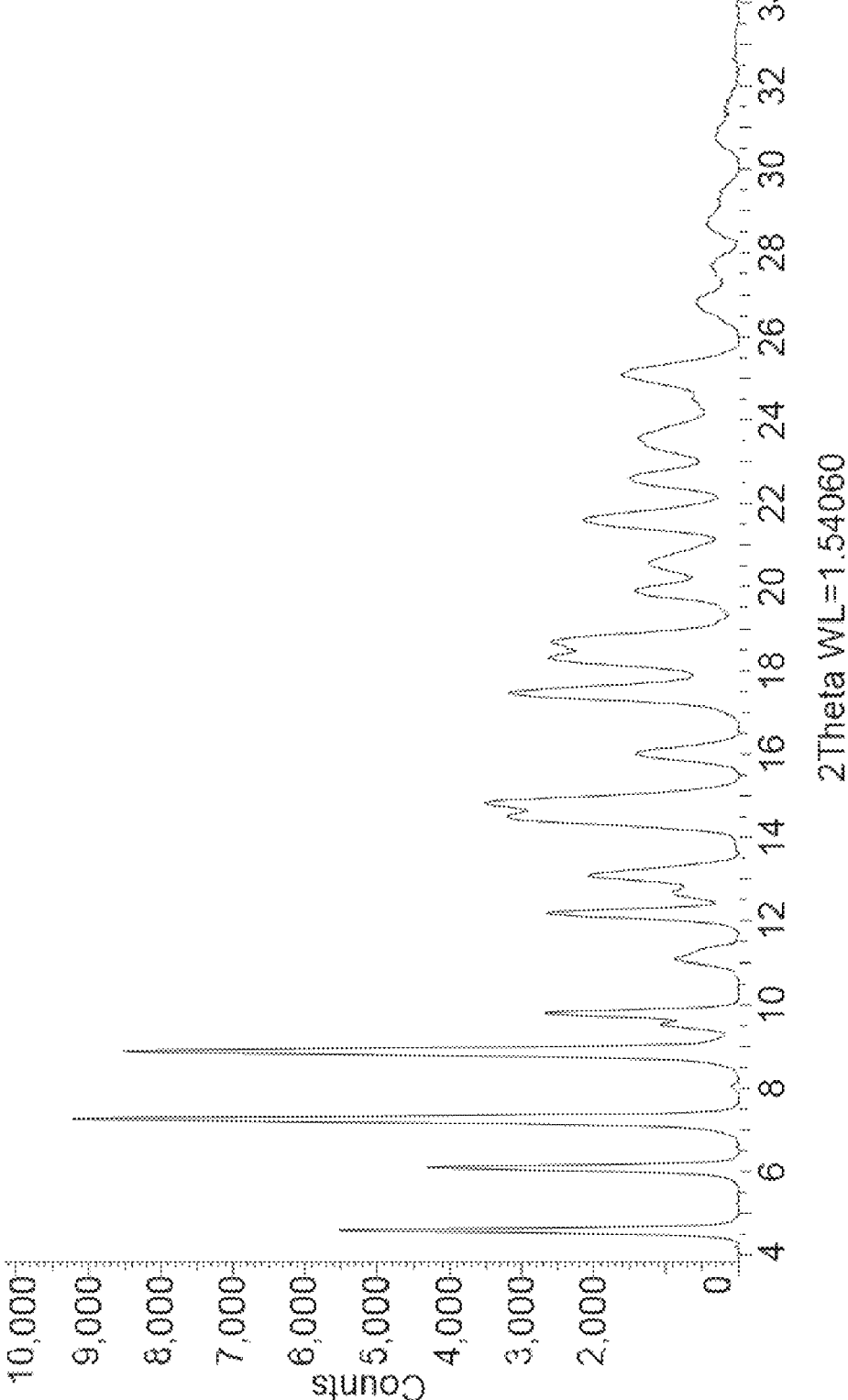
FIG. 11 is a representative PXRD diffractogram of remdesivir maleate Form I.

An illustrative PXRD diffractogram of remdesivir maleate Form I, as prepared in Example 9, is shown in FIG. 11. A peak listing, comprising representative peaks from the PXRD diffractogram in FIG. 11, and their relative intensities, is provided in Table 9. Although illustrative of the PXRD diffractogram that is provided for the remdesivir maleate Form I of the present invention, the relative intensities of the peaks are variable. Thus, depending on a particular sample, the prominence or relative intensity of the peaks observed may differ from those in the illustrative PXRD diffractogram and peak listing.

TABLE 9

| Relative peak intensities of remdesivir maleate Form I from FIG. 11 | |
| Angle (2θ) | Relative intensity (%) |
| --- | --- |
| 4.62 | 58.2 |
| 6.15 | 41.8 |
| 7.33 | 100 |
| 9 | 93.3 |
| 9.91 | 28.6 |
| 11.22 | 10.9 |
| 12.37 | 26.6 |
| 13.29 | 20.9 |
| 14.74 | 39.7 |
| 15.09 | 42.1 |
| 16.28 | 17.8 |
| 17.78 | 45.5 |
| 18.64 | 39.2 |
| 19.01 | 31.9 |
| 20.28 | 25.5 |
| 20.97 | 14.6 |
| 21.99 | 33.7 |
| 22.96 | 22.6 |
| 23.82 | 18.6 |
| 25.56 | 25.6 |

In another embodiment of the present invention, the processes provide a salt of remdesivir, remdesivir oxalate Form APO-I, wherein the molar ratio of remdesivir to oxalic acid is approximately 1:1.

Remdesivir oxalate Form APO-I can be characterized by a PXRD diffractogram comprising, among other peaks, characteristic peaks, expressed in degrees 2θ (±0.2°), at 7.4°, 10.3° and 22.9°. Preferably, the PXRD diffractogram further comprises at least three peaks, expressed in degrees 2θ (±0.2°), selected from the group consisting of 9.7°, 11.4°, 12.1°, 17.1°, 18.6°, 20.2° and 21.7°. More preferably, the PXRD diffractogram further comprises peaks, expressed in degrees 2θ (±0.2°), at 9.7°, 11.4°, 12.1°, 17.1°, 18.6°, 20.2° and 21.7°.

Figure 12:
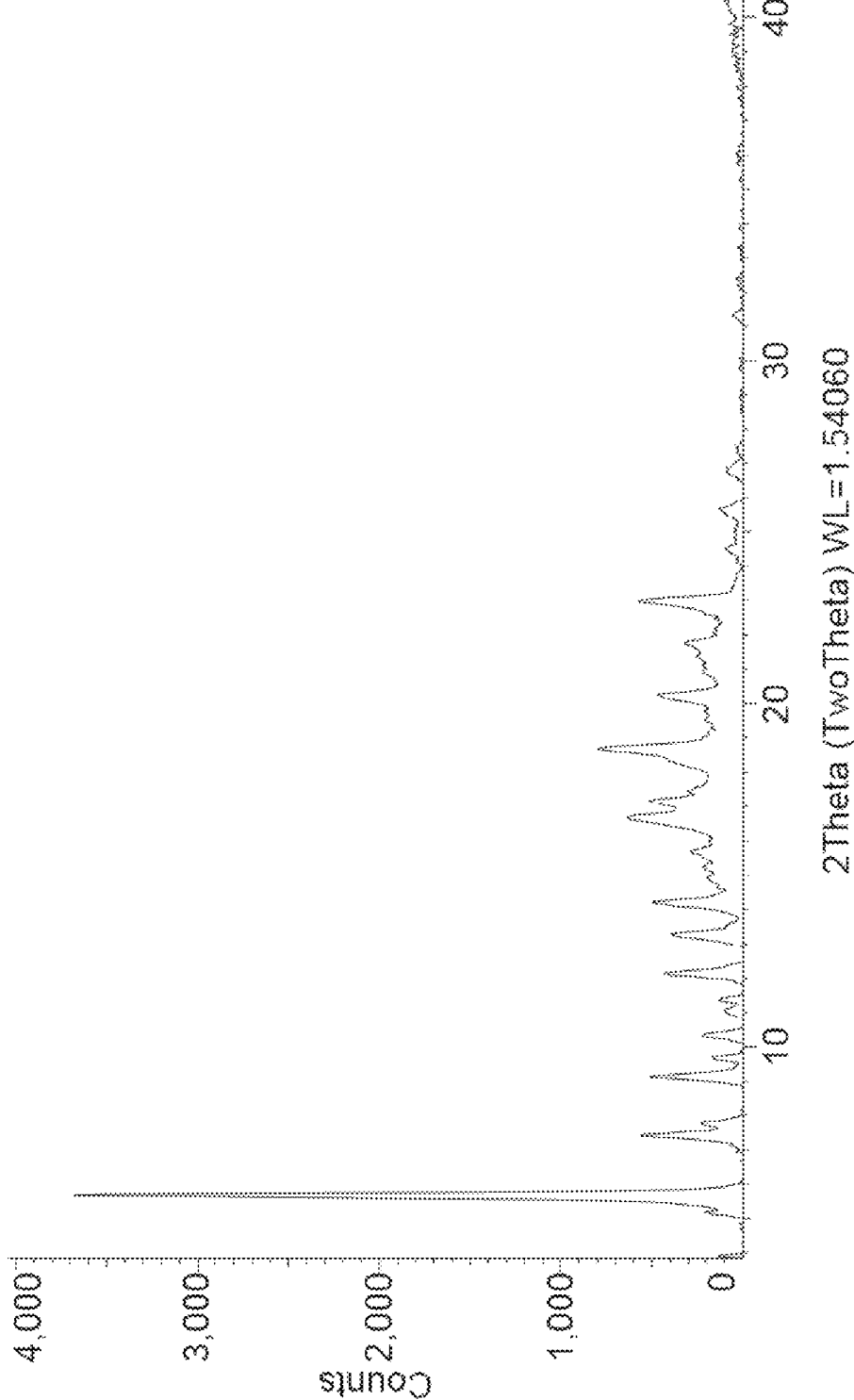
FIG. 12 is a representative PXRD diffractogram of remdesivir oxalate Form APO-I.

An illustrative PXRD diffractogram of remdesivir oxalate Form APO-I, as prepared in Example 10, is shown in FIG. 12. A peak listing, comprising representative peaks from the PXRD diffractogram in FIG. 12, and their relative intensities, is provided in Table 10. Although illustrative of the PXRD diffractogram that is provided for the remdesivir oxalate Form APO-I of the present invention, the relative intensities of the peaks are variable. Thus, depending on a particular sample, the prominence or relative intensity of the peaks observed may differ from those in the illustrative PXRD diffractogram and peak listing.

TABLE 10

| Relative peak intensities of remdesivir oxalate Form APO-I from FIG. 12 | |
| --- | --- |
| Angle (2θ) | Relative intensity (%) |
| 7.41 | 90.4 |
| 9.66 | 29.2 |
| 10.31 | 50.5 |
| 11.38 | 35.6 |
| 12.13 | 28.7 |
| 16.68 | 21.5 |
| 17.10 | 69.8 |
| 18.64 | 44.2 |
| 20.16 | 51.6 |
| 21.67 | 26.8 |
| 22.88 | 100.0 |

In another embodiment of the present invention, the processes provide a salt of olanzapine, olanzapine nicotinate, as described in Ravikumar et al. *Acta Cryst.* 2005, E61, o2720-o2723.

Olanzapine nicotinate can be characterized by a PXRD diffractogram comprising, among other peaks, characteristic peaks, expressed in degrees 2θ (±0.2°), at 8.1°, 13.5° and 20.9°. Preferably, the PXRD diffractogram further comprises at least three peaks, expressed in degrees 2θ (±0.2°), selected from the group consisting of 8.8°, 9.5°, 12.4°, 15.6°, 16.2°, 16.7°, 19.1°, 23.4°, 23.9° and 29.3°. More preferably, the PXRD diffractogram further comprises peaks, expressed in degrees 2θ (±0.2°), at 8.8°, 9.5°, 12.4°, 15.6°, 16.2°, 16.7°, 19.1°, 23.4°, 23.9° and 29.3°.

Figure 13:
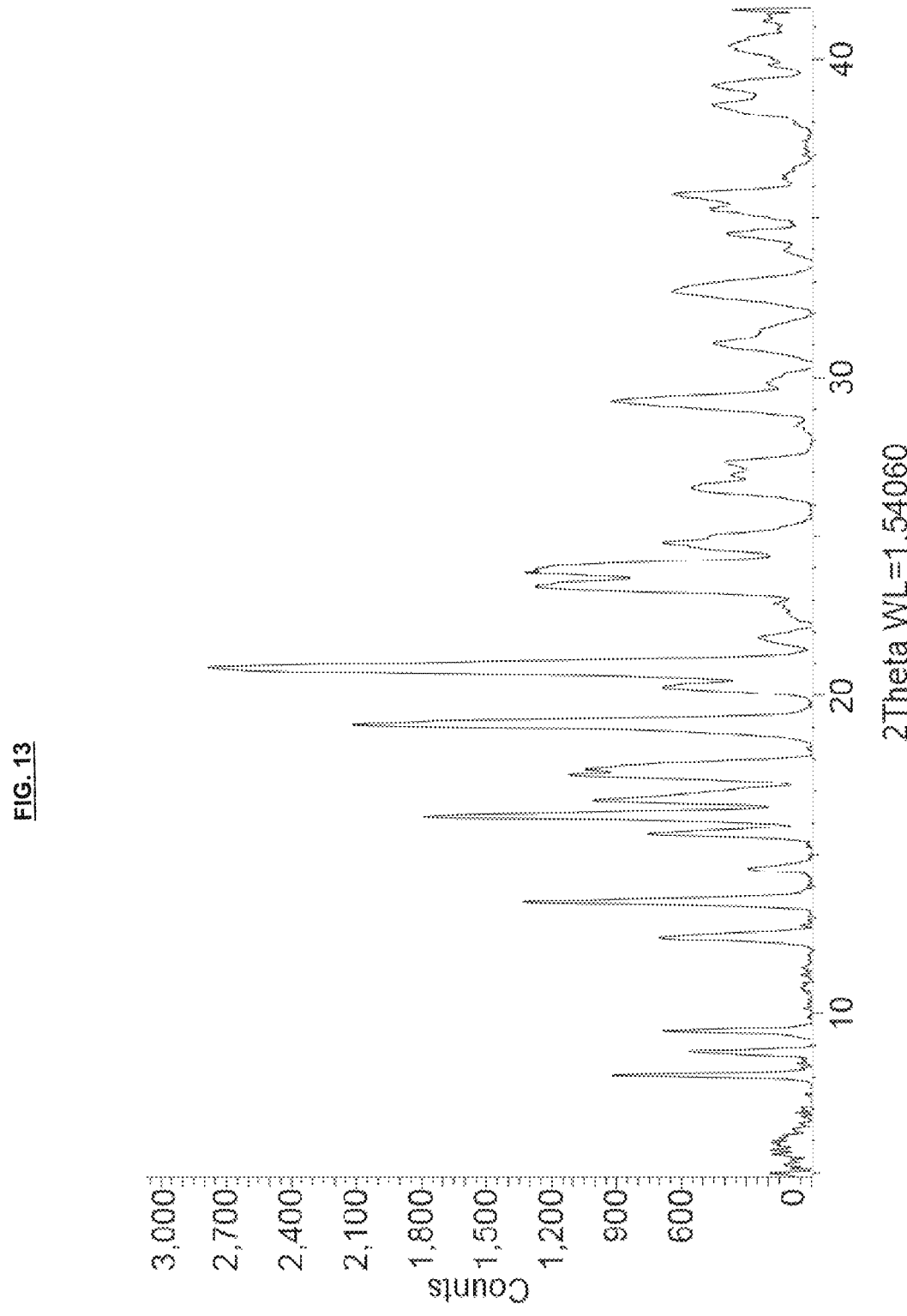
FIG. 13 is a representative PXRD diffractogram of olanzapine nicotinate.

An illustrative PXRD diffractogram of olanzapine nicotinate, as prepared in Example 11, is shown in FIG. 13. A peak listing, comprising representative peaks from the PXRD diffractogram in FIG. 13, and their relative intensities, is provided in Table 11. Although illustrative of the PXRD diffractogram that is provided for the olanzapine nicotinate of the present invention, the relative intensities of the peaks are variable. Thus, depending on a particular sample, the prominence or relative intensity of the peaks observed may differ from those in the illustrative PXRD diffractogram and peak listing.

TABLE 11

| Relative peak intensities of olanzapine nicotinate from FIG. 13 | |
| --- | --- |
| Angle (2θ) | Relative intensity (%) |
| 8.06 | 43.0 |
| 8.81 | 20.4 |
| 9.46 | 23.5 |
| 12.38 | 22.9 |
| 13.52 | 47.2 |
| 14.55 | 8.0 |
| 15.64 | 22.2 |
| 16.20 | 63.6 |
| 16.70 | 31.5 |
| 17.60 | 27.0 |
| 19.09 | 73.2 |
| 20.27 | 19.0 |
| 20.88 | 100.0 |
| 23.44 | 36.5 |
| 23.92 | 34.0 |
| 24.81 | 17.9 |
| 29.25 | 21.3 |

EXAMPLES

The following non-limiting examples are illustrative of some of the aspects and embodiments of the invention described herein.

The starting solid forms of the APIs used as a starting materials in the following examples was as follows: Form IV remdesivir (reported in WO 2018/204198 A1), Form III acalabrutinib (reported in WO 2017/002095 A1), Form C ibrutinib (reported in WO 2013/184572 A1), Form A tetrabenazine (reported in WO 2012/081031 A1), Form 2 lesinurad (reported in WO 2012/092395 A2), and lumacaftor having a PXRD diffractogram comprising, among other peaks, characteristic peaks, expressed in degrees 2θ (±0.2°), at 8.7°, 9.6° 14.8°, 17.3° and 19.1°. Starting solid forms of the coformers were as follows: nicotinamide (CCDC: NICOAM)—Wright, W. B; King, G. S. D. *Acta Cryst.* 1954, 7, 283-288, DOI: 10.1107/50365110X54000795, urea (CCDC: UREAXX)—Sklar, N.; Senko, M. E.; Post, B. *Acta Cryst.* 1961, 14, 716-720, DOI: and quercetin dihydrate (CCDC: FEFBEX)—Rossi, M.; Rickles, L.; Halpin, W. *Bioorg. Chem.* 1986, 14, 55-69, DOI: 10.1016/0045-2068 (86)90018-0. Starting solid forms of acids were as follows: maleic acid (CCDC: MALIAC): Shahat, M. *Acta Cryst.* 1952, 5, 763-768, DOI: 10.1107/50365110X52002082, oxalic acid (CCDC: OXALAC02): Cox, E. G.; Dougill, M. W.; Jeffrey, G. A. *J. Chem. Soc.* 1952, 4854-4864, DOI: 10.1039/JR9520004854, and naphthalene-2-sulfonic acid hydrate having a PXRD diffractogram comprising, among other peaks, expressed in degrees 2θ (±0.2°), at 9.4°, 13.6°, 14.6°, 15.3°, 18.1° and 18.9° (ACROS Organics™). Each of the references cited herein is hereby incorporated by reference.

PXRD Analysis:

PXRD diffractograms shown in FIGS. 3, 4, 6, 7, and 9-12 were recorded on a Bruker D8 Discover powder X-ray diffractometer (Bruker-AXS, Karlsruhe, Germany). The sample holder was oscillated along X and Y axes during the measurement. The generator was a Micro-focus X-ray source (IMSTube: Cu tube with 1.54184 A) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

PXRD diffractograms shown in FIGS. 5 and 8 were acquired on a PANanalytical X-Pert Pro MPD diffractometer with fixed divergence slits and an X'Celerator RTMS detector. The diffractometer was configured in Bragg-Brentano geometry; data was collected over a 2-theta range of 3° to 40° using CuKα radiation at a power of 40 mA and 45 kV. CuKβ radiation was removed using a divergent beam nickel filter. A step size of 0.017° was used. Samples were rotated to reduce preferred orientation effects. Samples were lightly ground prior to analysis.

Example 1: Preparation of Acalabrutinib Form APO-II

A round bottomed flask containing a 2 cm long stir bar was charged with acalabrutinib (1.31 g, 2.81 mmol) and nicotinamide (1.31 g, 10.7 mmol) and was attached to a rotary evaporator (Buchi Rotavapor® R-114) via a standard bump trap containing acetone solvent. The acetone solvent level was below the level of the drain holes of the trap to avoid liquid solvent from entering the vial. Vacuum was applied to the rotary evaporator until bubbling of acetone was observed, after which vacuum was discontinued and the system was allowed to equilibrate in the presence of solvent vapour. The contents of the flask were mixed by rotating the flask at room temperature at approximately 30 rpm for 4 days to afford acalabrutinib form APO-II. The PXRD of the resulting solid was consistent with that provided in FIG. 3.

Example 2: Preparation of Acalabrutinib Form APO-V

The process of this example was conducted in an apparatus analogous to that depicted in FIG. 1. In particular, the apparatus comprised a cylindrical glass jar (vessel 1) having an inlet (aperture 15) on one side wall and an outlet (aperture 16) diametrically opposed on the opposite side wall. The hollow shaft 13 on the inlet side comprised a short section of Tygon® tubing extending through the inlet of the vessel on its first end and joined on its second end with a hollow glass tube passing through a rotary evaporator motor (Buchi Rotovapor®) which was in turn joined to the first end of a cylindrical hollow fitting holding a bearing (11) to allow rotation of the vessel about a retort stand (fixed support structure 3) attached to the hollow fitting. The second end of the cylindrical hollow fitting was joined to a section of Tygon® tubing (line 17+25) attached to the arm of a gas bubbler adaptor extending into the headspace of a conical flask (solvent reservoir 30) containing ethanol. Another section of Tygon® tubing (line 23+24) extended from a nitrogen source and was attached to the other arm of the gas bubbler which was immersed in the ethanol. Valves 26 and 27 were not employed in this configuration. The hollow shaft 14 on the outlet side comprised a short piece of Tygon® tubing extending through the outlet on its first end and joined on its second end with the first end of a cylindrical hollow fitting which held a bearing (12) to allow rotation of the vessel about a retort stand (fixed support structure 3) attached to the hollow fitting. The second end of the cylindrical hollow fitting was joined with a section of Tygon® tubing (line 18) which extended into an oil bubbler (28). The open ends of the Tygon® tubing extending into the vessel interior (chamber 2) were covered with a small piece of filter cloth (filter 29) and the tubing was surrounded with parafilm to create a seal around the inlet and outlet. The axis of rotation of the rotary apparatus was substantially horizontal (+/−10°).

Acalabrutinib (10.00 g, 21.5 mmol) and finely powdered urea (1.94 g, 32.3 mmol) were added to the jar, which was fitted with a lid (loading/discharge port 9). A gentle nitrogen stream (approximately 60 cm 3 min$^{-1}$) was allowed to pass through the lines joining the ethanol solvent reservoir, the jar, and the bubbler while the jar was rotated at room temperature at approximately 30 rpm for a period of 18 hours, after which the flow of solvent vapour was exchanged for a nitrogen stream. The contents of the jar were further dried under a flow of nitrogen for one hour to afford acalabrutinib Form APO-V. The PXRD of a sample prepared by this method was consistent with that provided in FIG. 4.

Example 3: Preparation of Ibrutinib Form APO-II

A glass vial containing ibrutinib (1.0 g, 0.227 mmol) and methyl benzoate (143 μL, 1.13 mmol) was mixed in the presence of acetone vapour using the apparatus described in Example 1 at approximately 30 rpm for 48 hours to afford ibrutinib Form APO-II. The PXRD of the resulting solid was consistent with that provided in FIG. 5.

Example 4: Preparation of Ibrutinib Form APO-V

Ibrutinib (100 mg, 0.227 mmol) and methyl nicotinate (16 mg, 0.117 mmol) were lightly ground separately in a mortar and pestle prior to adding to a glass vial along with a small stir bar acting as a de-lumper. The contents of the vial were mixed in the presence of acetone vapour using the apparatus described in Example 1 at room temperature and approximately 30 rpm for 18 hours to afford ibrutinib Form APO-V. The PXRD of the resulting solid was consistent with that provided in FIG. 6.

Repetition of the same procedure but omitting the stir bar and solvent vapour did not result in detectable conversion to ibrutinib Form APO-V after 5 days. Resuming the mixing after addition of a stir bar in the absence of solvent vapour for a further week did not result in detectable conversion to ibrutinib Form APO-V.

Example 5: Preparation of Tetrabenazine Form APO-I

Tetrabenazine (100 mg, 0.315 mmol) and quercetin (107 mg, 0.354 mmol) were lightly ground separately in a mortar and pestle prior to adding to a glass vial along with two 5 mm diameter zirconia balls as de-lumpers. The contents of the vial were mixed in the presence of acetone vapour using the apparatus described in Example 1 at room temperature and approximately 30 rpm for 18 hours to afford tetrabenazine Form APO-I. The PXRD of the resulting solid was consistent with that provided in FIG. 7.

Example 6: Preparation of Lesinurad Form APO-III

Lesinurad (100 mg, 0.247 mmol) and nicotinamide (30 mg, 0.246 mmol) were lightly ground separately in a mortar and pestle prior to adding to a glass vial along with a small stir bar acting as a de-lumper. The contents of the vial were mixed in the presence of acetone vapour using the apparatus described in Example 1 at room temperature and approximately 30 rpm for 18 hours to afford lesinurad Form APO-Ill. The PXRD of the resulting solid was consistent with that provided in FIG. 8.

Repetition of the same procedure but omitting the stir bar and solvent vapour did not result in detectable conversion to lesinurad Form APO-III after 5 days. Resuming the mixing after addition of a stir bar in the absence of solvent vapour for a further week did not result in detectable conversion to lesinurad Form APO-Ill.

Example 7: Preparation of Lumacaftor Form APO-I

Lumacaftor (100 mg, 0.221 mmol) and nicotinamide (54 mg, 0.442 mmol) were lightly ground separately in a mortar and pestle prior to adding to a glass vial along with a small stir bar acting as a de-lumper. The contents of the vial were mixed in the presence of acetone vapour using the apparatus described in Example 1 at room temperature and approximately 30 rpm for 18 hours to afford lumacaftor Form APO-I. The PXRD of the resulting solid was consistent with that provided in FIG. 9.

Repetition of the same procedure but omitting the stir bar and solvent vapour did not result in detectable conversion to lumacaftor Form APO-I after 5 days. Resuming the mixing after addition of a stir bar in the absence of solvent vapour for a further week did not result in detectable conversion to lumacaftor Form APO-I.

Example 8: Preparation of Remdesivir Napsylate Form APO-I

Remdesivir (50 mg, 0.083 mmol) and naphthalene-2-sulfonic acid hydrate (18.1 mg, 0.0.087 mmol) were lightly ground separately in a mortar and pestle prior to adding to a glass vial with a 0.5 cm stir bar acting as a de-lumper. The contents of the vial were mixed in the presence of ethyl acetate vapour using the apparatus described in Example 1 at room temperature and approximately 30 rpm for 18 hours to afford remdesivir napsylate Form APO-I having the PXRD shown in FIG. 10.

Example 9: Preparation of Remdesivir Maleate Form I

Remdesivir (200 mg, 0.33 mmol) and maleic acid (43.4 mg, 0.37 mmol) were lightly ground separately in a mortar and pestle prior to adding to a glass vial with a 0.5 cm stir bar acting as a de-lumper. The contents of the vial were mixed in the presence of acetone vapour using the apparatus described in Example 1 at room temperature and approximately 30 rpm for 18 hours to afford remdesivir maleate Form I having the PXRD shown in FIG. 11.

Example 10: Preparation of Remdesivir Oxalate Form APO-I

Remdesivir (100 mg, 0.17 mmol) and oxalic acid (17.0 mg, 0.19 mmol) were lightly ground separately in a mortar and pestle prior to adding to a glass vial with a 0.5 cm stir bar acting as a de-lumper. The contents of the vial were mixed in the presence of acetone vapour using the apparatus described in Example 1 at room temperature and approximately 30 rpm for 18 hours to afford remdesivir oxalate Form APO-I having the PXRD shown in FIG. 12.

Example 11: Preparation of Olanzapine Nicotinate

Olanzapine (1.00 g, 3.20 mmol) and nicotinic acid (0.34 mg, 3.20 mmol) were lightly ground separately in a mortar and pestle prior to adding to a round bottomed flask along with a 1.5 cm stir bar acting as a de-lumper. The contents of the flask were mixed in the presence of methanol vapour using the apparatus described in Example 1 at room temperature and approximately 30 rpm for 18 hours to afford olanzapine nicotinate having the PXRD shown in FIG. 13.

What is claimed is:

1. A process for the preparation of an existing crystalline solid form comprising an active pharmaceutical ingredient and a distinct pharmaceutically acceptable entity, wherein the existence of the crystalline solid form has been confirmed prior to conducting the process, the process comprising mixing, in the presence of solvent vapour, of:
   (i) the active pharmaceutical ingredient in solid form; and
   (ii) the pharmaceutically acceptable entity, in solid or liquid form,
   wherein the entity has a melting point greater than approximately 30° C. or a boiling point greater than approximately 150° C. and the pharmaceutically acceptable entity and active pharmaceutical ingredient are incorporated in the same crystalline lattice,
   wherein the mixing is conducted in a rotary apparatus by means of rotation of a vessel containing the active pharmaceutical ingredient and the entity about its own axis,
   wherein the rotary apparatus comprises:
   a fixed support structure;
   a vessel rotatably supported by the fixed support structure about an axis and defining a chamber for mixing of the active pharmaceutical ingredient and the entity;
   an aperture in the vessel enabling communication between the chamber and a source of solvent vapour; and
   means for rotating the vessel about the axis.

2. The process of claim 1, wherein the solvent vapour is delivered through a first aperture in the vessel and evacuated through a second aperture in the vessel that is spaced from the first aperture.

3. The process of claim 1, wherein the entity is a coformer and the crystalline solid form is a multiple-component crystalline form.

4. A process for the preparation of an existing crystalline solid form comprising an active pharmaceutical ingredient and a distinct pharmaceutically acceptable entity, wherein the existence of the crystalline solid form has been confirmed prior to conducting the process, the process comprising mixing, in the presence of solvent vapour, of:
   (i) the active pharmaceutical ingredient in solid form; and
   (ii) the pharmaceutically acceptable entity, in solid or liquid form,
   wherein the entity has a melting point greater than approximately 30° C. or a boiling point greater than approximately 150° C. and the pharmaceutically acceptable entity and active pharmaceutical ingredient are incorporated in the same crystalline lattice,
   wherein the entity is an acid and the crystalline solid form is a salt,
   wherein the active pharmaceutical ingredient is an amine and the acid has a melting point greater than approximately 30° C., and
   wherein the acid is selected from the group consisting of fumaric acid, maleic acid, L-malic acid, succinic acid, citric acid, L-tartaric acid, oxalic acid, and naphthalene-2-sulfonic acid.

5. The process of claim 3, wherein the multiple-component crystalline form is selected from the group consisting of:
   (i) a cocrystal of acalabrutinib and urea;
   (ii) a cocrystal of acalabrutinib and nicotinamide;
   (iii) a solvate of ibrutinib and methyl benzoate;
   (iv) a cocrystal of ibrutinib and methyl nicotinate;

(v) a cocrystal of tetrabenazine and quercetin;

(vi) a cocrystal of lesinurad and nicotinamide; and (vii) a cocrystal of lumacaftor and nicotinamide.

6. The process of claim 5, wherein the multiple-component crystalline form is a cocrystal of acalabrutinib and urea having a molar ratio of acalabrutinib to urea of approximately 1:2.

7. The process of claim 5, wherein the multiple-component crystalline form is a cocrystal of acalabrutinib and nicotinamide having a molar ratio of acalabrutinib to nicotinamide of approximately 1:2.

8. The process of claim 5, wherein the multiple-component crystalline form is a solvate of ibrutinib and methyl benzoate having a molar ratio of ibrutinib to methyl benzoate of approximately 1:0.5.

9. The process of claim 5, wherein the multiple-component crystalline form is a cocrystal of ibrutinib and methyl nicotinate having a molar ratio of ibrutinib to methyl nicotinate of approximately 1:0.5.

10. The process of claim 5, wherein the multiple-component crystalline form is a cocrystal of tetrabenazine and quercetin having a molar ratio of tetrabenazine to quercetin of approximately 1:1.

11. The process of claim 4, wherein the active pharmaceutical ingredient is remdesivir and the entity is selected from the group consisting of maleic acid, oxalic acid, and naphthalene-2-sulfonic acid.

12. The process of claim 11, wherein the salt is a napsylate salt of remdesivir having a molar ratio of remdesivir to naphthalene-2-sulfonic acid of approximately 1:1.

13. The process of claim 11, wherein the salt is a maleate salt of remdesivir.

14. The process of claim 11, wherein the salt is an oxalate salt of remdesivir.

* * * * *